(12) United States Patent
Dorai

(10) Patent No.: US 7,820,159 B2
(45) Date of Patent: Oct. 26, 2010

(54) MN/CA IX AND EGFR PATHWAY INHIBITION

(75) Inventor: Thambi Dorai, Nanuet, NY (US)

(73) Assignee: Institute of Virology of the Slovak Academy of Sciences, Bratislava (SK)

( * ) Notice: Subject to any disclaimer, the term of this patent is extended or adjusted under 35 U.S.C. 154(b) by 0 days.

(21) Appl. No.: 11/927,150

(22) Filed: Oct. 29, 2007

(65) Prior Publication Data

US 2008/0112960 A1  May 15, 2008

Related U.S. Application Data

(60) Provisional application No. 60/855,507, filed on Oct. 31, 2006.

(51) Int. Cl.
*A61K 39/395* (2006.01)
*A61K 31/535* (2006.01)
*A61K 31/40* (2006.01)
*C07D 413/02* (2006.01)
*C07D 239/72* (2006.01)

(52) U.S. Cl. .............. 424/130.1; 424/146.1; 424/178.1; 514/235.5; 514/414; 544/121; 544/283

(58) Field of Classification Search ................... None
See application file for complete search history.

(56) References Cited

U.S. PATENT DOCUMENTS

| | | | |
|---|---|---|---|
| 5,387,676 A | | 2/1995 | Zavada et al. |
| 6,297,041 B1 * | | 10/2001 | Zavada et al. ................ 435/232 |
| 6,548,496 B2 * | | 4/2003 | Wissner et al. ........... 514/234.5 |
| 6,864,286 B2 * | | 3/2005 | Uckun et al. ................ 514/521 |
| 7,115,715 B2 * | | 10/2006 | Zavada et al. ............ 530/387.2 |
| 7,378,091 B2 * | | 5/2008 | Gudas et al. ............. 424/130.1 |
| 7,384,940 B2 * | | 6/2008 | Agus ........................ 514/228.2 |
| 2005/0031623 A1 * | | 2/2005 | Pastorek et al. .......... 424/155.1 |
| 2008/0038251 A1 * | | 2/2008 | Pastorekova et al. ..... 424/130.1 |

FOREIGN PATENT DOCUMENTS

| WO | WO 93/18152 | 9/1993 |
|---|---|---|
| WO | WO 95/34650 | 12/1995 |
| WO | WO 96/40210 | * 12/1996 |
| WO | WO 00/24913 | 5/2000 |
| WO | WO 03/100029 | 12/2003 |

OTHER PUBLICATIONS

Wong et al, Clinical Therapeutics 27(6): 684-694, 2005.*
Stadler et al, Cancer 104: 2323-2333, Dec. 2005.*
Staehler et al, Current Drug Targets 6(7): 835-846, Nov. 2005.*
Giaccone et al, Annals of Oncology 16: 538-548, 2005.*
Verma et al, Nature 389: 239-242, Sep. 1997.*
Harari et al, Endocrine-Related Cancer 11: 689-708, Dec. 2004.*
Wilhelm et al, Cancer Res 64: 7099-7109, Oct. 2004.*
Klire et al, Bioorganic & Medicinal Chemistry Letter 14: 783-786, Feb. 2004.*
Post et al, Clinical Cancer Research 10: 8603-8612, Dec. 2004.*
Uemura et al, British J Cancer 81(4): 741-746, Oct. 1999.*
Mendelsohn et al, J Clinical Oncology 21(14): 2787-2799, Jul. 2003.*
Kopacek et al, Biochimica et Biophysica Acta 1729: 41-49, 2005, abstract only.*
Stadler et al, Current Drug Targets 6(7): 835-846, 2005.*
Rubyani et al, Molecular Aspects of Medicine 22: 113-142, 2001.*
Stancoviski et al, Proceedings of the National Academy of Science USA 88: 8691-8695, 1991.*
Riemer et al, Mol. Immunol. 42: 1121-1124, 2005.*
Cochran et al, J. Immunol. Meth. 287: 147-158, 2004.*
Bardos and Ashcroft, "Hypoxia-inducible factor-1 and oncogenic signalling," *BioEssays*, 26.3: 262-269 (2004).
Chia et al., "Prognositc Significance of a Novel Hypoxia-Regulated Marker, Carbonic Anhydrase IX, in Invasive Breast Carcinoma," *Journal of Clinical Oncology*, 19(16): 3660-3668 (Aug. 15, 2001).
Christina et al., "Biodistribution and Pharmacokinetics of 125I-Labeled Monoclonal Antibody M75 Specific for Carbonic Anhydrase IX, an Intrinsic Marker of Hypoxia, in Nude Mice Xenografted with Human Colorectal Carcinoma," *Int. J. Cancer*: 105: 873-881 (2003).
Dorai et al., "The role of carbonic anhydrase IX overexpression in kidney cancer," *European Journal of Cancer*, 41: 2935-2947 (2005).
Dorai et al., "Role of Carbonic Anhydrases in the Progression of Renal Cell Carcinoma Subtypes: Proposal of a Unified Hypothesis," *Cancer Investigation*, 24: 754-779 (2006).
Giatromanolaki et al., "Expression of Hypoxia-inducible Carbonic Anhydrase-9 Relates to Angiogenic Pathways and Independently to Poor Outcome in Non-Small Cell Lung Cancer," *Cancer Research*, 61: 7992-7998 (Nov. 1, 2001).
Goethals et al., "Hypoxia in Human Colorectal Adenocarcinoma: Comparison Between Extrinsic and Potential Intrinsic Hypoxia Markers," *Int. J. Radiation Oncology Biol. Phys.*, 65(1): 246-254 (2006).

(Continued)

*Primary Examiner*—Phuong Huynh
(74) *Attorney, Agent, or Firm*—Leona L. Lauder; Joan C. Harland; Barbara A. Shimei

(57) ABSTRACT

The invention is based upon the discovery that the EGFR pathway can stimulate a previously unknown tumorigenic function of CA IX, via phosphorylation of the sole tyrosine residue present in CA IX's intracellular domain. EGFR-phosphorylated CA IX then interacts with the p85 subunit of PI3K to activate Akt, which in turn is associated with anti-apototic function and increased cell survival. The latter finding indicates that there is a positive feedback loop for CA9 expression mediated by the PI3K pathway in preneoplastic/neoplastic diseases. Disclosed herein are novel therapeutic methods for treating preneoplastic/neoplastic diseases associated with abnormal MN/CA IX expression, using EGFR pathway inhibitors. Preferably, the EGFR pathway inhibitors are tyrosine kinase inhibitors or EGFR-specific antibodies. Further disclosed are methods for patient therapy selection for EGFR pathway inhibitors, preferably in combination with other cancer therapies, based on detection of abnormal MN/CA9 gene expression in preneoplastic/neoplastic tissues.

4 Claims, 8 Drawing Sheets

OTHER PUBLICATIONS

Gollob, J.A., "Sorafenib: Scientific Rationales for Single-Agent and Combination Therapy in Clear-Cell Renal Cell Carcinoma," *Clinical Genitourinary Cancer*, 4(3): 167-174 (2005).

Gollob et al., "Role of Raf Kinase in Cancer: Therapeutic Potential of Targeting the Raf/MEK/ERK Signal Transduction Pathway," *Seminars in Oncology*, 33(4): 392-406 (2006).

Haddad, J.J., "Hypoxia and the regulation of mitogen-activated protein kinases: gene transcription and the assessment of potential pharmacologic therapeutic interventions," *International Immunopharmacology*, 4: 1249-1285 (2004).

Harris, A.L., "Hypoxia—A Key Regulatory Factor in Tumour Growth," *Nature Reviews*, 2: 38-47 (Jan. 2002).

Ihnatko et al., "Extracellular acidosis elevates carbonic anhydrase IX in human glioblastoma cells via transcriptional modulation that does not depend on hypoxia," *International Journal of Oncology*, 29: 1025-1033 (2006).

Ivanov et al., "Expression of Hypoxia-Inducible Cell-Surface Transmembrane Carbonic Anhydrases in Human Cancer," *American Journal of Pathology*, 158(3): 905-919 (Mar. 2001).

Kaluz et al., "Lowered Oxygen Tension Induces Expression of the Hypoxia Marker MN/Carbonic Anhydrase IX in the Absence of Hypoxia-inducible Factor 1alpha Stabilization: A Role for Phosphatidylinositol 3'-Kinase," *Cancer Research*, 62: 4469-4477 (Aug. 1, 2002).

Kopacek et al., "MAPK pathway contributes to density- and hypoxia-induced expression of the tumor-associated carbonic anhydrase IX," *Biochimica et Biophysica Acta*, 1729: 41-49 (2005).

Lam et al., "Renal Cell Carcinoma 2005: New Frontiers in Staging, Prognostication and Targeted Molecular Therapy," *Journal of Urology*, 173: 1853-1862 (Jun. 2005).

Lam et al., "Novel approaches in the therapy of metastatic renal cell carcinoma," *World J. Urol.*, 23: 202-212 (2005).

Liao et al., "Identification of the MN/CA9 Protein As a Reliable Diagnostic Biomarker of Clear Cell Carcinoma of the Kidney," *Cancer Research*, 57: 2827-2831 (Jul. 15, 1997).

Marshall, J., "Clinical Implications of the Mechanism of Epidermal Growth Factor Receptor Inhibitors," *Cancer*, 107(6): 1207-1218 (Sep. 15, 2006).

McKiernan et al., "Expression of the Tumor-associated Gene *MN*: A Potential Biomarker for Human Renal Cell Carcinoma," *Cancer Research*, 57: 2362-2365 (Jun. 15, 1997).

Opavsky et al., "Human *MN/CA9* Gene, a Novel Member of the Carbonic Anhydrase Family: Structure and Exon to Protein Domain Relationships," *Genomics*, 33: 480-487 (1996).

Pastorek et al., "Cloning and characterization of MN, a human tumor-associated protein with a domain homologous to carbonic anhydrase and a putative helix-loop-helix DNA binding segment," *Oncogene*, 9: 2877-2888 (1994).

Pastorekova and Pastorek, "MN/CA IX and MAPK Inhibition," U.S. Appl. No. 11/726,065, filed Mar. 20, 2007).

Pastorekova and Zavada, "Carbonic anhydrase IX (CA IX) as a potential target for cancer thereapy," *Cancer Therapy*, 2: 245-262 (2004).

Patard et al., "Understanding the Importance of Smart Drugs in Renal Cell Carcinoma," *European Urology*, 49: 633-643 (2006).

Robertson et al., "Role of Carbonic Anhydrase IX in Human Tumor Cell Growth, Survival, and Invasion," *Cancer Research*, 64: 6160-6165 (Sep. 1, 2004).

Said, J., "Biomarker discovery in urogenital cancer," *Biomarkers*, 10(Supp. 1): S83-S86 (Nov. 2005).

Sorenson et al., "Influence of oxygen concentration and pH on expression of hypoxia induced genes," *Radiotherapy and Oncology*, 76: 187-193 (2005).

Svastova et al., "Carbonic anhydrase IX reduces E-cadherin-mediated adhesion of MDCK cells via interaction with beta-catenin," *Experimental Cell Research*, 290: 332-345 (2003).

Svastova et al., "Hypoxia activates the capacity of tumor-associated carbonic anhydrase IX to acidify extracellular pH," *FEBS Letters*, 577: 439-445 (2004).

Swinson et al., "Coexpression of epidermal growth factor receptor with related factors is associated with a poor prognosis in non-small-cell lung cancer," *British Journal of Cancer*, 91: 1301-1307 (2004).

Swinson et al., "Carbonic Anhydrase IX Expression, a Novel Surrogate Marker of Tumor Hypoxia, Is Associated With a Poor Prognosis in Non-Small-Cell Lung Cancer," *Journal of Clinical Oncology*, 21(3): 473-482 (Feb. 1, 2003).

Swinson et al., "Hypoxia-Inducible Factor-1alpha in Non Small Cell Lung Cancer: Relation to Growth Factor, Protease and Apoptosis Pathways," *Int. J. Cancer*, 111: 43-50 (2004).

Van Den Eynden et al., "Validation of a tissue microarray to study differential protein expression in inflammatory and non-inflammatory breast cancer," *Breast Cancer Research and Treatment*, 85: 13-22 (2004).

Wykoff et al., "Hypoxia-inducible Expression of Tumor-associated Carbonic Anhydrases," *Cancer Research*, 60: 7075-7083 (Dec. 15, 2000).

Guinn and Mulherkar, "International Progress in Cancer Gene Therapy," *Cancer Gene Therapy*, 15: 765-775 (2008).

Duan et al., "A tumor targeted gene vector modified with G250 monoclonal antibody for gene therapy," *J. Control Release*, 127(2): 173-179 (Apr. 21, 2008; Epub Feb. 8, 2008) Abstract only.

Gura, T., "Systems for Identifying New Drugs Are Often Faulty," *Science*, 278: 1041-1042 (Nov. 7, 1997).

Hernandez et al., "Novel kidney cancer immunotherapy based on the granulocyte-macrophage colony-stimulating factor and carbonic anhydrase IX fusion gene," *Clin. Cancer Res.*, 9(5): 1906-1916 (May 2003) Abstract only.

Jongmans et al., "Targeting of adenovirus to human renal cell carcinoma cells," *Urology*, 62(3): 559-565 (Sep. 2003) Abstract only.

Lim et al., "Tumor-specific gene therapy for uterine cervical cancer using MN/CA9-directed replication-competent adenovirus," *Cancer Gene Ther.*, 11(8): 532-538 (Aug. 2004) Abstract only.

Mukouyama et al., "Generation of kidney Cancer-specific antitumor immune responses using peripheral blood monocytes transduced with a recombinant adenovirus encoding carbonic anhydrase 9," *Clin. Cancer Res.*, 10(4): 1421-1429 (Feb. 15, 2004) Abstract only.

Ou et al., "A potential for tissue restrictive gene therapy in renal cell carcinoma using MN/CA IX promoter," *Anticancer Res.*, 25(2A): 881-886 (Mar.-Apr. 2005) Abstract only.

Siena et al., "Biomarkers Predicting Clinical Outcome of Epidermal Growth Factor Receptor-Targeted Therapy in Metastatic Colorectal Cancer," *JNCI Advance Access*: 1-17 (Sep. 8, 2009).

* cited by examiner

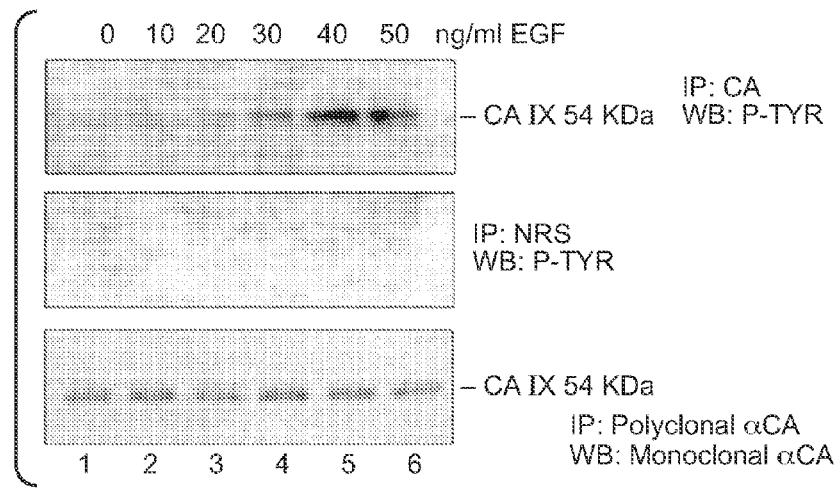
FIG. 1A
FIG. 1B
FIG. 1C
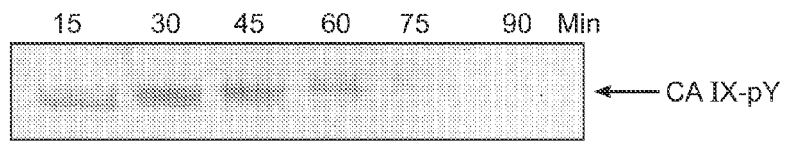
FIG. 1D

| | | | | | | | | | | | | |
|---|---|---|---|---|---|---|---|---|---|---|---|---|
| 1 | | | | | M | A | P | L | C | P | L | 12 |
| 1 | ACA | GTC | AGC | CGC | ATG | GCT | CCC | CTG | TGC | CCC | CTG | 48 |
| 13 | L | I | P | A | P | A | P | G | L | T | V | L | S | 28 |
| 49 | TTG | ATC | CCG | GCC | CCT | GCT | CCA | GGC | CTC | ACT | GTG | CTC | TCA | 96 |
| 29 | L | L | L | M | P | V | H | Q | R | L | M | Q | 44 |
| 97 | CTG | CTG | CTT | CTG | ATG | CCT | GTC | CAT | CAG | AGG | TTG | ATG | CAG | 144 |
| 45 | E | D | S | P | L | G | G | G | S | S | P | L | 60 |
| 145 | GAG | GAT | TCC | CCC | CTG | GGA | GGA | GGA | AGT | TCT | CCC | CCA | CTG | 192 |
| 61 | G | E | E | D | L | P | S | E | E | D | P | E | D | 76 |
| 193 | GGG | GAG | GAG | GAT | CTG | CCC | AGT | GAA | GAG | GAT | CCC | GAG | GAT | 240 |
| 77 | P | P | L | E | G | E | L | P | E | S | R | E | E | 92 |
| 241 | CCA | CCC | CTA | GAG | GGA | GAG | CTA | CCT | GAG | TCA | AGA | GAG | GAG | 288 |
| 93 | E | D | L | P | E | V | K | P | K | S | E | E | E | 108 |
| 289 | GAG | GAT | CTA | CCT | GAA | GTT | AAG | CCT | AAA | TCA | GAA | GAG | GAG | 336 |
| 109 | K | L | E | D | L | P | T | V | E | A | P | G | D | 124 |
| 337 | AAG | TTA | GAG | GAT | CTA | CCT | ACT | GTT | GAG | GCT | CCT | GGA | GAT | 384 |
| 125 | P | Q | N | N | A | H | R | D | K | P | W | S | Q | 140 |
| 385 | CCC | CAG | AAT | AAT | GCC | CAC | AGG | GAC | AAA | CCC | TGG | TCC | CAG | 432 |
| 141 | W | R | Y | G | D | P | P | W | R | V | S | A | H | 156 |
| 433 | TGG | CGC | TAT | GGA | GAC | CCG | CCC | CGG | GTG | TCC | GCC | CAT | 480 |
| 157 | A | G | R | F | Q | S | P | V | D | I | R | P | Q | 172 |
| 481 | GCG | GGC | CGC | TTC | CAG | TCC | CCG | GTG | GAT | ATC | CGC | CCC | CAG | 528 |

| 173 | F   | C   | P   | A   | L   | R   | P   | L   | E   | L   | L   | G   | F   | Q   | L   | P   | 188 |
| 529 | TTC | TGC | CCG | GCC | CTG | CGC | CCC | CTG | GAA | CTC | CTG | GGC | TTC | CAG | CTC | CCG | 576 |
| 189 | P   | L   | P   | E   | L   | R   | L   | N   | A   | H   | S   | V   | Q   | L   | 204 |
| 577 | CCG | CTC | CCA | GAA | CTG | CGC | CTG | AAT | GCT | CAC | AGT | GTG | CAA | CTG | 624 |
| 205 | T   | L   | P   | Q   | L   | G   | L   | A   | L   | G   | E   | R   | E   | Y   | 220 |
| 625 | ACC | CTG | CCT | CAG | CTA | GGG | CTG | GCT | CTG | GGG | GAG | CGG | GAG | TAC | 672 |
| 221 | R   | A   | Q   | L   | H   | L   | H   | W   | G   | A   | A   | R   | P   | G   | 236 |
| 673 | CGG | GCT | CAG | CTG | CAT | CTG | CAC | TGG | GGG | GCA | GCT | CGT | CCC | GGC | 720 |
| 237 | S   | E   | H   | T   | V   | E   | G   | R   | F   | P   | A   | E   | I   | H   | 252 |
| 721 | TCG | GAG | CAC | ACT | GTG | GAA | GGG | CGT | TTC | CCT | GCC | GAG | ATC | CAC | 768 |
| 253 | V   | H   | L   | S   | T   | A   | F   | A   | R   | V   | D   | E   | A   | L   | G   | R   | 268 |
| 769 | GTT | CAC | CTC | AGC | ACC | GCC | TTT | GCC | AGA | GTT | GAC | GAG | GCC | TTG | GGG | CGC | 816 |
| 269 | P   | G   | G   | L   | A   | V   | L   | A   | F   | L   | E   | E   | G   | P   | E   | 284 |
| 817 | CCG | GGA | GGC | CTG | GCC | GTG | TTG | GCC | TTT | CTG | GAG | GAG | GGC | CCG | GAA | 864 |
| 285 | E   | N   | S   | A   | Y   | E   | Q   | L   | S   | R   | L   | E   | E   | I   | A   | 300 |
| 865 | GAA | AAC | AGT | GCC | TAT | GAG | CAG | TTG | TCT | CGC | CTG | GAG | GAA | ATC | GCT | 912 |
| 301 | E   | G   | S   | E   | T   | Q   | P   | G   | L   | D   | I   | S   | A   | L   | 316 |
| 913 | GAG | GGC | TCA | GAG | ACT | CAG | CCA | GGA | CTG | GAC | ATA | TCT | GCA | CTC | 960 |
| 317 | L   | P   | S   | D   | F   | S   | R   | Y   | F   | Q   | Y   | E   | G   | S   | L   | T   | 332 |
| 961 | CTG | CCC | TCT | GAC | TTC | AGC | CGC | TAC | TTC | CAA | TAT | GAG | GGG | TCT | CTG | ACT | 1008 |
| 333 | T   | P   | P   | C   | A   | Q   | G   | V   | I   | W   | T   | V   | F   | N   | Q   | T   | 348 |
| 1009 | ACA | CCG | CCC | TGT | GCC | CAG | GGT | GTC | ATC | TGG | ACT | GTG | TTT | AAC | CAG | ACA | 1056 |

FIG. 6C

| | | | | | | | | | | | | | | | | |
|---|---|---|---|---|---|---|---|---|---|---|---|---|---|---|---|---|
| 349 | V | M | L | S | A | K | Q | L | H | T | L | S | D | T | L | W | 364 |
| 1057 | GTG | ATG | CTG | AGT | GCT | AAG | CAG | CTC | CAC | ACC | CTC | TCT | GAC | ACC | CTG | TGG | 1104 |
| 365 | G | P | G | D | S | R | L | Q | L | N | F | R | A | T | Q | P | 380 |
| 1105 | GGA | CCT | GGT | GAC | TCT | CGG | CTA | CAG | CTG | AAC | TTC | CGA | GCG | ACG | CAG | CCT | 1152 |
| 381 | L | N | G | R | V | I | E | A | S | F | P | A | G | V | D | S | 396 |
| 1153 | TTG | AAT | GGG | CGA | GTG | ATT | GAG | GCC | TCC | TTC | CCT | GCT | GGA | GTG | GAC | AGC | 1200 |
| 397 | S | P | R | A | A | E | P | V | Q | L | N | S | C | L | A | A | 412 |
| 1201 | AGT | CCT | CGG | GCT | GCT | GAG | CCA | GTC | CAG | CTG | AAT | TCC | TGC | CTG | GCT | GCT | 1248 |
| 413 | G | D | I | L | A | V | F | G | L | L | F | A | V | T | S | 428 |
| 1249 | GGT | GAC | ATC | CTA | GCC | GTT | TTT | GGC | CTC | CTT | TTT | GCT | GTC | ACC | AGC | 1296 |
| 429 | V | A | F | L | V | Q | M | R | R | Q | H | R | A | G | R | 444 |
| 1297 | GTC | GCG | TTC | CTT | GTG | CAG | ATG | AGA | AGG | CAG | CAC | AGA | GCC | GGA | AGG | 1344 |
| 445 | G | G | V | S | Y | R | P | A | E | V | A | E | T | G | A | * | 460 |
| 1345 | GGG | GGT | GTG | AGC | TAC | CGC | CCA | GCA | GAG | GTA | GCC | GAG | ACT | GGA | GCC | TAG | 1392 |
| 1393 | AGG | CTG | GAT | CTT | GGA | GAA | TGT | GAG | AAG | CCA | AGA | GGC | ATC | TGA | | | 1440 |
| 1441 | GGA | GCC | GGT | AAC | TGT | GTC | CTC | CTG | CTC | ATT | CCT | CTT | TGA | GGG | | | 1488 |
| 1489 | TGC | CAA | GAA | ATT | TTT | TAA | AAT | AAA | TAT | TTA | TAA | T | | | | | 1522 |

FIG. 6

MN/CA IX AND EGFR PATHWAY INHIBITION

This application claims priority from U.S. Provisional Application No. 60/855,507 filed Oct. 31, 2006.

FIELD OF THE INVENTION

The present invention is in the general area of medical genetics and in the fields of biochemical engineering, immunochemistry and oncology. More specifically, it relates to the MN gene—a cellular gene considered to be an oncogene, known alternatively as MN/CA9, CA9, or carbonic anhydrase 9, which gene encodes the oncoprotein now known alternatively as the MN protein, the MN/CA IX isoenzyme, MN/CA IX, carbonic anhydrase IX, CA IX, the MN/G250 or the G250 protein.

More specifically, the instant invention is based upon the discovery of a potential tumorigenic role of MN/CA IX's intracellular domain (IC): the sole tyrosine moiety of MN/CA IX present in its IC domain can be phosphorylated in an EGFR-dependent manner and leads to activation of Akt. As the Akt pathway has a distinct antiapoptotic function, that discovery has important applications for the therapy of preneoplastic/neoplastic diseases characterized by abnormal MN/CA9 gene expression, and for making clinical decisions on cancer treatment.

BACKGROUND OF THE INVENTION

As indicated above, the MN gene and protein are known by a number of alternative names, which names are used herein interchangeably. The MN protein was found to bind zinc and have carbonic anhydrase (CA) activity and is now considered to be the ninth carbonic anhydrase isoenzyme—MN/CA IX or CA IX [Opavsky et al., *Genomics*, 33: 480-487 (1996)]. According to the carbonic anhydrase nomenclature, human CA isoenzymes are written in capital roman letters and numbers, whereas their genes are written in italic letters and arabic numbers. Alternatively, "MN" is used herein to refer either to carbonic anhydrase isoenzyme IX (CA IX) proteins/polypeptides, or carbonic anhydrase isoenzyme 9 (CA9) gene, nucleic acids, cDNA, mRNA etc. as indicated by the context.

The MN protein has also been identified with the G250 antigen. Uemura et al. [*J. Urol.* 157 (4 Suppl.): 377 (Abstract 1475; 1997)] states: "Sequence analysis and database searching revealed that G250 antigen is identical to MN, a human tumor-associated antigen identified in cervical carcinoma (Pastorek et al., 1994)."

Zavada et al., International Publication No. WO 93/18152 (published Sep. 16, 1993) and U.S. Pat. No. 5,387,676 (issued Feb. 7, 1995) describe the discovery of the MN gene and protein. The MN gene was found to be present in the chromosomal DNA of all vertebrates tested, and its expression to be strongly correlated with tumorigenicity. In general, oncogenesis may be signified by the abnormal expression of MN/CA IX protein. For example, oncogenesis may be signified: (1) when MN/CA IX protein is present in a tissue which normally does not express MN/CA IX protein to any significant degree; (2) when MN/CA IX protein is absent from a tissue that normally expresses it; (3) when CA9 gene expression is at a significantly increased level, or at a significantly reduced level from that normally expressed in a tissue; or (4) when MN/CA IX protein is expressed in an abnormal location within a cell. WO 93/18152 further discloses, among other MN-related inventions, MN/CA IX-specific monoclonal antibodies (MAbs), including the M75 MAb and the VU-M75 hybridoma that secretes the M75 MAb. The M75 MAb specifically binds to immunodominant epitopes on the proteoglycan (PG) domain of the MN/CA IX proteins.

Zavada et al., International Publication No. WO 95/34650 (published Dec. 21, 1995) provides in FIG. 1 the nucleotide sequences for a full-length MN cDNA [also provided herein in FIG. 6 (SEQ ID NO: 1)] clone isolated as described therein, and the amino acid sequence [also provided herein in FIG. 6 (SEQ ID NO: 2)] encoded by that MN cDNA. WO 95/34650 also provides in FIG. 6 the nucleotide sequence for the MN promoter [SEQ ID NO: 24]. Those MN cDNA, promoter and amino acid sequences are incorporated by reference herein.

Zavada et al., International Publication No. WO 03/100029 (published Dec. 4, 2003) discloses among other MN-related inventions, MN/CA IX-specific MAbs that are directed to non-immunodominant epitopes, including those on the carbonic anhydrase (CA) domain of the MN/CA IX protein. An example of such a MN/CA IX-specific MAb is the V/10 MAb, secreted from the V/10-VU hybridoma.

The MN protein is now considered to be the first tumor-associated carbonic anhydrase isoenzyme that has been described. The carbonic anhydrase family (CA) includes eleven catalytically active zinc metalloenzymes involved in the reversible hydration-dehydration of carbon dioxide: $CO_2 + H_2O \Leftrightarrow HCO_3^- + H^+$. CAs are widely distributed in different living organisms. The CAs participate in a variety of physiological and biological processes and show remarkable diversity in tissue distribution, subcellular localization, and biological functions [Parkkila and Parkkila, Scand *J Gastroenterol.*, 31: 305-317 (1996); Potter and Harris, *Br J Cancer*, 89: 2-7 (2003); Wingo et al., *Biochem Biophys Res Commun.* 288: 666-669 (2001)]. Carbonic anhydrase IX, CA IX, is one of the most recently identified isoenzymes [Opavsky et al., *Genomics*, 33: 480-487 (1996); Pastorek et al., *Oncogene*, 9: 2877-2888 (1994)]. Because of the CA IX overexpression in transformed cell lines and in several human malignancies, it has been recognized as a tumor-associated antigen and linked to the development of human cancers [Zavada et al., *Int. J. Cancer*, 54: 268-274 (1993); Liao et al., *Am. J. Pathol.*, 145: 598-609 (1994); Saarnio et al., *Am Pathol*, 153: 279-285 (1998)].

MN/CA IX is a glycosylated transmembrane CA isoform with a unique N-terminal proteoglycan-like extension. Through transfection studies it has been demonstrated that MN/CA IX can induce the transformation of 3T3 cells [Opavsky et al., *Genomics*, 33: 480-487 (1996); Pastorek et al., *Oncogene*, 9: 2877-2888 (1994)].

The MN protein was first identified in HeLa cells, derived from a human carcinoma of cervix uteri. Many studies, using the MN-specific monoclonal antibody (MAb) M75, have confirmed the diagnostic/prognostic utility of MN in diagnosing/prognosing precancerous and cancerous cervical lesions [Liao et al., *Am. J. Pathol.*, 145: 598-609 (1994); Liao and Stanbridge, *Cancer Epidemiology Biomarkers & Prevention*, 5: 549-557 (1996); Brewer et al., *Gynecologic Oncology* 63: 337-344 (1996)]. Immunohistochemical studies with the M75 MAb of cervical carcinomas and a PCR-based (RT-PCR) survey of renal cell carcinomas have identified MN expression as closely associated with those cancers and confirm MN's utility as a tumor biomarker [Liao et al., *Am. J. Pathol.*, 145: 598-609 (1994); Liao and Stanbridge, *Cancer Epidemiology, Biomarkers & Prevention*, 5: 549-557 (1996); McKiernan et al., *Cancer Res.* 57: 2362-2365 (1997)]. In various cancers (notably uterine cervical, ovarian, endometrial, renal, bladder, breast, colorectal, lung, esophageal, head and neck and prostate cancers, among others), MN/CA IX expression is increased and has been correlated with microvessel density and the levels of hypoxia in some tumors [Koukourakis et al., *Clin Cancer Res*, 7: 3399-3403 (2001); Giatromanolaki et al., *Cancer Res*, 61: 7992-7998 (2001)].

In tissues that normally do not express MN protein, MN/CA IX positivity is considered to be diagnostic for pre-neoplastic/neoplastic diseases, such as, lung, breast and cervical precancers/cancers [Swinson et al., *J Clin Oncol*, 21: 473-482 (2003); Chia et al., *J Clin Oncol*, 19: 3660-3668 (2001); Loncaster et al., *Cancer Res*, 61: 6394-6399 (2001)], among other precancers/cancers. Very few normal tissues have been found to express MN protein to any significant degree. Those MN-expressing normal tissues include the human gastric mucosa and gallbladder epithelium, and some other normal tissues of the alimentary tract. Paradoxically, MN gene expression has been found to be lost or reduced in carcinomas and other preneoplastic/neoplastic diseases in some tissues that normally express MN, e.g., gastric mucosa.

MN Regulation Under Hypoxia and Normoxia

Strong association of MN/CA IX with a broad range of tumors is principally related to its transcriptional regulation by hypoxia and high cell density, which appear to activate the MN/CA9 promoter through two different, but interconnected pathways [Wykoff et al., *Cancer Res.*, 60: 7075-7083 (2000); Lieskovska, et al., *Neoplasma*, 46: 17-24 (1999); Kaluz et al., *Cancer Res.*, 62: 4469-4477 (2002)]. Those two pathways are activated via stabilization of HIF-1α by hypoxia, and direct stimulation of MN/CA IX protein expression by the phosphotidylinositol-3-kinase (PI3K) pathway, respectively.

Hypoxia is a reduction in the normal level of tissue oxygen tension. It occurs during acute and chronic vascular disease, pulmonary disease and cancer, and produces cell death if prolonged. Pathways that are regulated by hypoxia include angiogenesis, glycolysis, growth-factor signaling, immortalization, genetic instability, tissue invasion and metastasis, apoptosis and pH regulation [Harris, A. L., *Nature Reviews*, 2: 38-47 (January 2002)].

The central mediator of transcriptional up-regulation of a number of genes during hypoxia is the transcription factor. HIF-1 is composed of two subunits: a constitutively expressed HIF-1β and a rate-limiting HIF-1α, which is regulated by the availability of oxygen. Under hypoxia, HIF-1α skips modification of its conserved proline and asparagine residues by oxygen-sensitive hydroxylases, thus avoiding degradation mediated by pVHL and inactivation mediated by FIH-1 (factor inhibiting HIF-1) [Maxwell et al., *Nature*, 399: 271-275 (1999); Jaakkola et al., *Science*, 292: 468-472 (2001); Ivan et al., *Science*, 292: 464-468, 2001; Jaakkola, et al., *Science*, 292: 468-472 (2001); Mahon, et al., *Genes Dev.*, 15: 2675-2686 (2001)]. This leads to HIF-1α accumulation, dimerization with HIF-1β, binding to hypoxia response element (HRE) sites in the target genes, interaction with the cofactors and stimulation of the HIF-1 trans-activation capacity.

In the absence of oxygen, HIF-1 binds to HIF-binding sites within HREs of oxygen-regulated genes, thereby activating the expression of numerous hypoxia-response genes, such as erythropoietin (EPO), and the proangiogenic growth factor vascular endothelial growth factor (VEGF). In addition, HIF-1α can be up-regulated under normoxic conditions by different extracellular signals and oncogenic changes transmitted via the PI3K and MAPK pathways [Semenza, *Biochem. Pharmacol.*, 64: 993-998 (2002); Bardos and Ashcroft, *BioEssays*, 26: 262-269 (2004)]. Whereas PI3K activation results in an increased level of HIF-1α protein, MAPK activation improves its trans-activation properties [Laughner, et al., *Mol. Cell. Biol.* 21: 3995-4004 (2001); Richard et al., *J. Biol. Chem.*, 274: 32631-32637 (1999)].

MN/CA IX was shown to be one of the most strongly hypoxia-inducible proteins, via the HIF-1 protein binding to the hypoxia-responsive element of the MN promoter [Wykoff et al., *Cancer Res*, 60: 7075-7083 (2000); Svastova et al., *Exp Cell Res*, 290: 332-345 (2003)]. Like other HIF-1-regulated genes, the transcription of the MN gene is negatively regulated by wild-type von Hippel-Lindau tumor suppressor gene [Ivanov et al., *Proc Natl Acad Sci* (USA), 95: 12596-12601 (1998)]. Low levels of oxygen lead to stabilization of HIF-1α, which in turn leads to the increased expression of MN [Wykoff et al., *Cancer Res*, 60: 7075-7083 (2000)]. Areas of high expression of MN in cancers are linked to tumor hypoxia as reported in many cancers, and incubation of tumor cells under hypoxic conditions leads to the induction of MN expression [Wykoff et al., *Cancer Res*, 60: 7075-7083 (2000); Koukourakis et al., *Clin Cancer Res*, 7: 3399-3403 (2001); Giatromanolaki et al., *Cancer Res*, 61: 7992-7998 (2001); Swinson et al., *J Clin Oncol*, 21: 473-482 (2003); Chia et al., *J Clin Oncol*, 19: 3660-3668 (2001); Loncaster et al., *Cancer Res*, 61: 6394-6399 (2001)].

Key elements of the MN/CA9 promoter are the HIF-1 and SP1 binding regions [Kaluz et al., *Cancer Res.* 63: 917-922 (2003)] [PR1-HRE element]. The MN/CA9 promoter sequence (−3/−10) between the transcription start and PR1 contains a HRE element recognized by a hypoxia inducible factor 1 (HIF-1), which governs transcriptional responses to hypoxia [Wykoff et al., *Cancer Res.* 60: 7075-7083 (2000)]. The promoter of the CA9 gene contains five regions protected in DNase I footprinting (PR1-PR5, numbered from the transcription start) [Kaluz et al., *J. Biol. Chem.*, 274: 32588-32595 (1999)]. PR1 and PR2 bind SP1/3 and AP1 transcription factors and are critical for the basic activation of CA9 transcription [Kaluz et al., *J. Biol. Chem.*, 274: 32588-32595 (1999); Kaluzova et al., *Biochem. J.*, 359: 669-677 (2001)]. HIF-1 strongly induces transcription of the CA9 gene in hypoxia, but for full induction requires a contribution of the SP1/3 transcription factor binding to PR1 [Wykoff et al., *Cancer Res.*, 60: 7075-7083 (2000); Kaluz, et al., *Cancer Res.*, 63: 917-922 (2003)].

Regulation under normoxia also requires SP1 [Kaluz et al., *Cancer Res.* 62: 4469-4477 (2002)]. Upregulation of CA9 transcription in increased cell density involves a mild pericellular hypoxia, depends upon cooperation of SP1 with HIF-1 at subhypoxic level and operates via the PI3K pathway [Kaluz et al., *Cancer Res.* 62: 4469-4477 (2002)]. Hypoxia and cell density act in an additive fashion so that the highest expression of CA9 is achieved under conditions of low oxygen at high density [Kaluz et al., *Cancer Res.*, 62: 4469-4477 (2002)].

MN's Intracellular Region and the EGFR Pathway

As indicated above, CA9 expression is upregulated by both HIF-1α- and PI3K-dependent pathways, and both the PG and CA extracellular domains of CA IX have predicted roles in tumorigenesis based on cell adhesion and carbonic anhydrase activities. The invention disclosed herein is based on the discovery of a potential tumorigenic role of a third CA IX domain, the intracellular domain (IC). The inventor discloses finding CA IX to be associated with EGFR in lipid rafts in RCC cell lines, and that the sole tyrosine moiety of CA IX present in its IC domain can be phosphorylated in an EGFR-dependent manner. The inventor found evidence that tyrosine-phosphorylated CA IX interacts with the regulatory subunit of PI3K (p85), resulting in activation of Akt. That finding indicates that there is a positive feedback loop for CA9 expression in RCC, mediated by the PI3K pathway, which may contribute to the aggressiveness of RCC. Based on those novel findings, the instant invention discloses therapeutic methods targeted to the EGFR pathway which can be used alone, or in combination with other MN-targeted methods, to treat preneoplastic/neoplastic diseases characterized by abnormal MN expression.

SUMMARY OF THE INVENTION

The subject invention is based upon the discovery of a potential tumorigenic role of the intracellular domain (IC) of CA IX: the sole tyrosine moiety present in the IC can be phosphorylated by the EGFR pathway, leading to CA IX interaction with the p85 regulatory subunit of PI3K and resulting in activation of Akt. As Akt activation has antiapoptotic effects, inhibiting phosphorylation of CA IX's intracellular domain is considered to have important consequences for tumor biology.

The subject invention concerns the identification of a site within the CA IX intracellular domain [SEQ ID NO: 7] comprising a tyrosine residue which can be phosphorylated in an EGFR-dependent manner. EGFR pathway inhibitors are then a new therapy for targeting tumors associated with abnormal CA9 expression, usually increased CA9 expression. Said EGFR pathway inhibitors may be targeted to any components of the EGFR pathway, including, for example, Ras, Raf, MEK, and ERK. Preferably, said EGFR pathway inhibitors are used in combination with other MN-targeted therapies, such as CA IX-specific antibodies, CA IX-specific carbonic anhydrase inhibitors, CA9 antisense therapies and/or PI3K-targeted therapies.

In one aspect, the instant invention is directed to a method of treating a mammal, preferably a human, for a preneoplastic/neoplastic disease, wherein said disease is characterized by abnormal MN/CA9 gene expression, comprising administering to said mammal a therapeutically effective amount of a composition comprising an EGFR pathway inhibitor. Preferably, said EGFR pathway inhibitor is an EGFR tyrosine kinase inhibitor or an anti-EGFR antibody. Preferably, said EGFR tyrosine kinase inhibitor is selected from gefitinib, erlotinib, lapatinib, canertinib and EKB-569, and said anti-EGFR antibody is selected from cetuximab, panitumumab, nimotuzumab, matuzumab, and MDX-447. Said EGFR pathway inhibitor may be administered in an unmodified form, or may be conjugated to an antibody or biologically active antibody fragment which specifically binds MN/CA IX. In one preferred embodiment of the invention, said EGFR pathway inhibitor is a bispecific antibody or antibody fragment having a specificity for EGFR and a specificity for MN/CA IX.

Preferably, said therapeutic methods further comprise administering to said mammal radiation and/or a therapeutically effective amount in a physiologically acceptable formulation of one or more of the following compounds selected from the group consisting of: conventional anticancer drugs, chemotherapeutic agents, different inhibitors of cancer-related pathways, bioreductive drugs, gene therapy vectors, CA9 antisense oligonucleotides and vectors, CA IX-specific inhibitors, CA IX-specific antibodies and CA IX-specific antibody fragments that are biologically active. Preferably, said inhibitors of cancer-related pathways are selected from HIF-1α targeted therapies, VEGF-R targeted therapies, IL-2 and interferon-α, inhibitors of the MAPK pathway, inhibitors of the PI3K pathway; and/or said gene therapy vectors are targeted to hypoxic tumors. Preferably, said inhibitor of the MAPK pathway is the bis aryl-urea Sorafenib (BAY 43-9006) or an omega-carboxypyridyl substituted urea. Most preferably, said inhibitor of the MAPK pathway is the bis aryl-urea Sorafenib (BAY 43-9006).

Said preneoplastic/neoplastic disease characterized by abnormal MN/CA9 gene expression can be that of many different tissues, for example, uterine, cervical, ovarian, endometrial, renal, bladder, breast, colorectal, lung, esophageal, and prostate, among many other tissues. Of particular interest are preneoplastic/neoplastic diseases of the breast, colon, rectum and of the urinary tract, as of the kidney, bladder and urethra. Renal cell carcinoma (RCC), and metastatic breast cancer are just a couple of representative disease characterized by abnormally high levels of MN/CA9 expression. Also, representative are mesodermal tumors, such as neuroblastomas and retinoblastomas; sarcomas, such as osteosarcomas and Ewing's sarcoma; melanomas; and gynecologic preneoplastic/neoplastic diseases, particularly, of the uterine cervix, endometrium and ovaries, more particularly, cervical squamous cell, adrenosquamous, and glandular preneoplastic/neoplastic diseases, including adenocarcinoma, cervical metaplasia, and condylomas.

Exemplary preneoplastic/neoplastic diseases characterized by abnormal MN/CA9 gene expression are selected from the group consisting of mammary, urinary tract, bladder, kidney, ovarian, uterine, cervical, endometrial, squamous cell, adenosquamous cell, vaginal, vulval, prostate, liver, lung, skin, thyroid, pancreatic, testicular, brain, head and neck, mesodermal, sarcomal, stomach, spleen, gastrointestinal, esophageal, and colon preneoplastic/neoplastic diseases. Preferably, said preneoplastic/neoplastic disease characterized by abnormal MN/CA9 gene expression is kidney cancer, most preferably, renal cell carcinoma. Said disease may be either a normoxic or a hypoxic tumor.

In a second aspect, the invention concerns a method of therapy selection for a human patient with a preneoplastic/neoplastic disease, comprising detecting and quantifying the level of MN/CA9 gene expression in a sample taken from the patient; and deciding to use EGFR pathway-directed therapy to treat the patient based upon abnormal levels of MN/CA9 gene expression in the patient's sample, usually based upon increased levels of MN/CA9 expression above normal MN/CA9 expression levels. Preferably, said EGFR pathway-directed therapy comprises the use of a tyrosine kinase inhibitor or an anti-EGFR antibody. Said EGFR pathway inhibitor may be administered in an unmodified form, or may be conjugated to an antibody or biologically active antibody fragment which specifically binds MN/CA IX. Said therapeutic methods may further comprise administering to said human one or more additional therapies; preferably, said additional therapies target MN/CA9 expression or MN/CA IX enzymatic activity. Said additional therapies may comprise the use of the bis aryl-urea Sorafenib (BAY 43-9006) or an omega-carboxypyridyl substituted urea. Most preferably, said additional therapy is the bis aryl-urea Sorafenib (BAY 43-9006).

Said preneoplastic/neoplastic sample would preferably be a tissue, cell or body fluid sample. A tissue sample could be, for example, a formalin-fixed, paraffin-embedded tissue sample or a frozen tissue sample, among other tissue samples. A body fluid sample could be, for example, a blood, serum, plasma or urine sample, among other body fluid samples.

Preferably, said detecting and quantifying step comprises immunologically detecting and quantifying the level of MN/CA IX protein in said sample, and may comprise the use of an assay selected from the group consisting of Western blots, enzyme-linked immunosorbent assays, radioimmunoassays, competition immunoassays, dual antibody sandwich assays, immunohistochemical staining assays, agglutination assays, and fluorescent immunoassays. Preferably, said immunologically detecting and quantifying comprises the use of the monoclonal antibody secreted by the hybridoma VU-M75 which has Accession No. ATCC HB 11128. Said detecting and quantifying step could also be envisioned as detecting and quantifying MN nucleic acids, such as, mRNA that expresses MN/CA IX, for example, using quantitative PCR or other methods known in the art.

REFERENCES

The following references are cited herein or provide updated information concerning the MN/CA9 gene and the MN/CA IX protein, and/or cancers associated with abnormal MN/CA9 gene expression. All the listed references as well as other references cited herein are specifically incorporated by reference.

1. Hock et al., *J Urol*, 167: 57-60 (2002).
2. Jemal et al., *CA-Cancer J Clin*, 52: 23-47 (2003).
3. Takahashi et al., *Oncogene*, 22: 6810-6818 (2003).
4. Higgins et al., *Am J Pathol*, 162: 925-932 (2003).
5. Reuter Jr, V. E., and Presti J. C., *Semin Oncol:* 27: 124-137 (2000).
6. Linehan, W. M., and Zbar, B., *Cancer Cell*, 6: 223-228 (2004).
7. McKiernan et al., *Cancer Res*, 57: 2362-2365 (1997).
8. Whittington et al., *Proc Natl Acad Sci* (USA), 98: 9545-9550 (2001).
9. Parkkila et al., *J Histochem Cytochem*, 48: 1601-1608 (2000).
10. Saarino et al., *J Hepatol*, 35: 643-649 (2001).
11. Turner et al., *Human Pathols* 28: 740-744 (1997).
12. Kivela et al., *Dig Dis Sci*, 46: 2179-2186 (2001).
13. Pantuck et al., *Clin Cancer Res*, 9: 4641-4652 (2003).
14. Potter and Harris, *Cell Cycle*, 3: 164-167 (2004).
15. Tripp et al., *J Biol Chem*, 276: 48615-48618 (2001).
16. Pastorek et al., *Oncogene*, 9: 2877-2888 (1994).
17. Parkkila S., "An overview of the distribution and function of carbonic anhydrases in mammals," In Chegwidden W R, Carter N, Edwards Y. eds. *The carbonic anhydrases: new horizons*, Basel, Switzerland, Birkhauser Verlag, 2000. pp. 76-93.
18. Murakami et al., *BJU Into*, 83: 743-747 (1999).
19. Ivanov et al., *Am J Pathol*, 158: 905-919 (2001).
20. Zhuang et al. *Mod Pathol*, 9: 838-842 (1999).
21. Ashida et al., *J Cancer Res Clin Oncol*, 128: 561-568 (2002).
22. Liao et al., *Cancer Res*, 57: 2827-2831 (1997).
23. Ivanov et al., *Proc Natl Acad Sci* (USA), 95: 12596-12601 (1998).
24. Maxwell et al., *Nature*, 399: 271-275 (1999).
25. Ivan et al., *Science*, 292: 464-468 (2001).
26. Jaakkola et al., *Science*, 292: 468-472 (2001).
27. Rohzim et al., *Cancer Res*, 54: 6517-6525 (1994).
28. Shi et al., *Oncogene*, 20: 3751-3756 (2001).
29. Lardner A., *J Leukoc Biol*, 69: 522-530 (2001).
30. Teicher et al., *Anti Cancer Res*, 13: 1549-1556 (1993).
31. Svastova et al., *Exp Cell Res*, 290: 332-345 (2003).
32. Beavon I R G., *J Clin Pathol Mol Pathol*, 52: 179-187 (1999).
33. Genda et al., *Lab Invest*, 80: 387-394 (2000).
34. Beltran P. J., and Bixby J. L., *Front Biosci*, 8: 287-299 (2003).
35. Barnea et al., *Mol Cell Biol*, 13: 1497-1506 (1993).
36. Peles et al., *Cell* 82: 251-260 (1995).
37. Potter C P S, and Harris A. L., *Brit J Cancer*, 89: 2-7 (2003).
38. Goebel et al., *Human Immunol*, 63: 813-820 (2002).
39. Zatovicova et al., *J Immunol Meth.* 282: 117-134 (2003).
40. Sun et al., *Biochemistry*, 41: 6338-6345 (2002).
41. Dancey, J. E., *J Clin Oncol*, 22: 2975-2977 (2004).
42. Vivanco, I., and Sawyers C. L., *Nat Rev Cancer*, 2: 489-501 (2002).
43. Vanhaesebroeck et al., *Trends Biochem Sci*, 22: 267-272 (1997).
44. Svastova et al., *FEBS Lett*, 577: 439-445 (2004).
45. Beasley et al., *Cancer Res*, 61: 5262-5267 (2001).
46. Olive et al., *Cancer Res*, 61: 8924-8929 (2001).
47. Richard et al., *J Biol Chem*, 275: 26765-26771 (2000).
48. Kaluz et al., *Cancer Res*, 62: 4469-4477 (2002).
49. Leek et al., *Brit J Cancer*, 79: 991-995 (1999).
50. Haddad J. J., and Land S. C., *FEBS Lett*, 505: 269-274 (2001).
51. Wykoff et al., *Cancer Res*, 60: 7075-7083 (2000).
52. Loncaster et al., *Cancer Res*, 61: 6394-6399 (2001).
53. Chia et al., *J Clin Oncol*, 19: 3660-3668 (2001).
54. Giatromalonaki et al., *Cancer Res*, 61: 7992-7998 (2001).
55. Moch et al., *Human Pathol*, 28: 1255-1259 (1997).
56. Uhlman et al., *Clin Cancer Res*, 1: 913-920 (1995).
57. Ramp et al., *J Urol*, 157: 2345-2350 (1997).
58. Nanjundan et al., *J Biol Chem*, 278: 37413-37418 (2003).
59. Chen X., and Resh M. D., *J Biol Chem*, 277: 49631-49637 (2002).
60. Schlessinger J., *Cell* 103: 211-225 (2000).
61. Yarden, Y., and Sliwkowski, M. Y., *Nat Rev Mol Cell Biol*, 2: 127-137 (2001).
62. Rordorf-Nikolic et al., *J Biol Chem*, 270: 3662-3666 (1995).
63. Hellyer et al., *Biochem J*, 333: 757-763 (1998).
64. Ponzetto et al., *Mol Cell Biol*, 13: 4600-4608 (1993).
65. Wu et al., *J Biol Chem*, 278: 40425-40428 (2003).
66. Sekulic A., *Cancer Res*, 60: 3504-3513 (2000).
67. Kozma S. C., and Thomas G., *BioEssays*, 24: 65-71 (2002).
68. Vogt P. K., *Trends Mol Med*, 7: 482-484 (2001).
69. Aoki et al., *Proc Natl Acad Sci* (USA), 98: 136-141 (2001).
70. Bjornsti M. A., and Houghton P. J., *Nat Rev Cancer*, 4: 335-348 (2004).
71. Abraham R. T., *Cell* 111: 9-12 (2002).
72. Page et al., *J Biol Chem*, 277: 48403-48409 (2002).
73. Hudson et al., *Mol Cell Biol*, 22: 7004-7014 (2002).
74. Philips et al., *J Biol Chem*, 280: 22473-22481 (2005).
75. Sterling et al., *J Biol Chem*, 277: 25239-25246 (2002).
76. Mekhail et al., *Nat Cell Biol*, 6: 642-647 (2004).
77. Perera et al., *Clin Cancer Res*, 6: 1518-1523 (2000).
78. Knebelmann et al., *Cancer Res*, 58: 226-231 (1998).
79. Pal et al., *J Biol Chem*, 272: 27509-27512 (1997).
80. Kawakami et al., *J Biol Chem*, 279: 47720-47725 (2004).

Abbreviations

The following abbreviations are used herein:

| | |
|---|---|
| aa | amino acid |
| Akt | protein kinase B (PKB) |
| αCA | antibody to CA IX |
| ATCC | American Type Culture Collection |
| bp | base pairs |
| CA | carbonic anhydrase |
| ° C. | degrees centigrade |
| CA IX-pY | tyrosine phosphorylated CA IX |
| DMSO | dimethyl sulfoxide |

-continued

| | |
|---|---|
| ECL | enhanced chemiluminescence method |
| EDTA | ethylenediaminetetraacetate |
| EGF | epidermal growth factor |
| EGFR | epidermal growth factor receptor |
| EPO | erythropoietin |
| ERK | extracellular signal-regulated kinase |
| FBS | fetal bovine serum |
| FIH-1 | factor inhibiting HIF-1 |
| HIF | hypoxia-inducible factor |
| HRE | hypoxia response element |
| HRP | horseradish peroxidase |
| IC | intracellular |
| IP | immunoprecipitation |
| kb | kilobase |
| kbp | kilobase pairs |
| kd or kDa | kilodaltons |
| M | molar |
| MAb | monoclonal antibody |
| MAPK | mitogen-activated protein kinase |
| MBS | MES buffered saline |
| MEK | mitogen/extracellular-signal-regulated kinase kinase, also known as map kinase kinase (MKK) |
| MEM | Minimum Essential Medium |
| MES | morpholinoethane sulfonic acid |
| min. | minute(s) |
| mg | milligram |
| ml | milliliter |
| mM | millimolar |
| NEAA | non-essential amino acids |
| ng | nanogram |
| nm | nanometer |
| nM | nanomolar |
| NRS | normal rabbit serum |
| NSCLC | non-small cell lung cancer |
| nt | nucleotide |
| ORF | open reading frame |
| pAkt | phosphorylated Akt |
| PCR | polymerase chain reaction |
| PG | proteoglycan |
| PI3K | phosphotidylinositol-3-kinase |
| pI | isoelectric point |
| PMSF | phenylmethyl sulfonyl fluoride |
| PTB | phosphotyrosine binding |
| P-TYR | phosphotyrosine |
| PVDF | polyvinylidene fluoride |
| RIPA | radioimmunoprecipitation assay |
| RT-PCR | reverse transcription polymerase chain reaction |
| SDS | sodium dodecyl sulfate |
| SDS-PAGE | sodium dodecyl sulfate-polyacrylamide gel electrophoresis |
| TKI | tyrosine kinase inhibitor |
| TM | transmembrane |
| Tris | tris (hydroxymethyl) aminomethane |
| μg | microgram |
| μl | microliter |
| μM | micromolar |
| VEGF | vascular endothelial growth factor |
| VEGF-R | vascular endothelial growth factor receptor |
| VHL | von Hippel-Lindau protein |
| WB | Western blot |

Cell Lines

| | |
|---|---|
| CGL3 | tumorigenic HeLa × normal fibroblast hybrid cells (HeLa D98/AH.2 derivative; express CA9, but level increased by both high density and hypoxia). |
| HeLa | aneuploid, epithelial-like cell line isolated from a human cervical adenocarcinoma [Gey et al., Cancer Res., 12: 264 (1952); Jones et al., Obstet. Gynecol., 38: 945-949 (1971)] obtained from Professor B. Korych, [Institute of Medical Microbiology and Immunology, Charles University; Prague, Czech Republic]. |

-continued

| | |
|---|---|
| SKRC-01 | human renal cell carcinoma (RCC) cell line overexpressing CA IX, provided by Dr. Neil Bander [Weill Medical College, Cornell University, NY]; cell line described in Cho et al., Mol. Carcinog., 27(3): 184-189 (2000). |
| SKRC-08 | human renal cell carcinoma (RCC) cell line overexpressing CA IX, provided by Dr. Neil Bander (supra). |
| SKRC-17 | human renal cell carcinoma (RCC) cell line which does not overexpress CA IX, provided by Dr. Neil Bander (supra). |

Nucleotide and Amino Acid Sequence Symbols

The following symbols are used to represent nucleotides herein:

| Base Symbol | Meaning |
|---|---|
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention may be used herein to identify said amino acids as follows:

| Amino acid name | 3 Ltr. Abbrev. | 1 Ltr. Abbrev. |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

BRIEF DESCRIPTION OF THE FIGURES

FIG. 1A-C depicts EGF dependent phosphorylation of membrane associated carbonic anhydrase IX. SKRC-01 cells were serum starved and stimulated with increasing concentrations of EGF for 30 min. Whole cell lysates were immunoprecipitated (IP) with polyclonal antibody to CA IX (CA) and the blots (WB) were probed with a monoclonal antibody to phosphotyrosine (P-TYR) (panel A). As a negative control, the same experiment was repeated with normal rabbit serum (NRS) instead of the polyclonal antibody to CA IX, shown in panel B. Panel C shows that equivalent amounts of protein were loaded when the same amounts of protein loaded for panel A were run on another gel and probed with the monoclonal antibody to CA IX (M75 MAb). FIG. 1D shows kinetics of the loss of phosphorylation of CA IX (CA IX-pY) in EGF stimulated SKRC-01 cells using conditions as in FIG. 1A-C. The initial EGF stimulus was removed after 30 min and the loss of CA IX-pY signal was followed up to 90 min.

FIG. 6A-C provides the nucleotide sequence for a MN cDNA [SEQ ID NO: 1] clone isolated. FIGS. 6 A-C also sets forth the predicted amino acid sequence [SEQ ID NO: 2] encoded by the cDNA.

DETAILED DESCRIPTION

Figure 2:
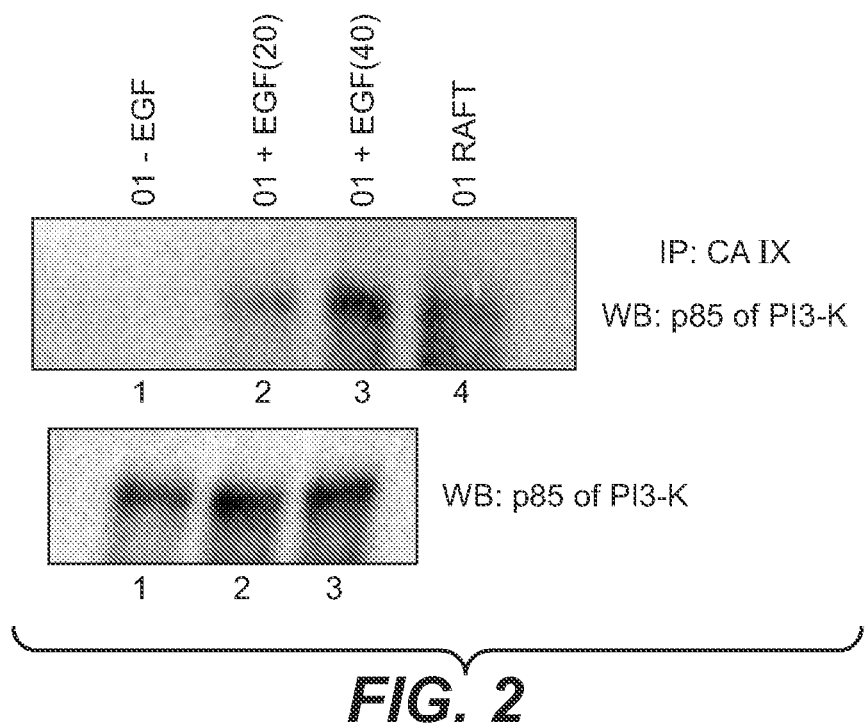
FIG. 2 depicts co-immunoprecipitation of p85 subunit of PI3K with the tyrosine phosphorylated CA IX. SKRC-01 cells stimulated in the presence or absence of EGF were solubilized and immunoprecipitated (IP) with M75 MAb to CA IX. The blots (WB) were probed with a polyclonal antibody to the p85 regulatory subunit of PI3K (upper panel lanes 1, 2 and 3). As a loading control, identical blots were probed for the presence of the total p85 subunit of PI3K (lower panel). In some cases, the lipid raft membrane fractions from EGF stimulated SKRC-01 cells were solubilized and processed for immunoprecipitation with CA IX and immunoblotting with p85 (upper panel, lane 4).

The MN/CA IX protein, via its CA and PG domains, is functionally implicated in tumorigenesis as part of the regulatory mechanisms that control pH and cell adhesion. However, it had been previously unknown whether MN/CA IX's IC domain had a potential tumorigenic role as well.

As shown in the Examples below, the inventor found that in RCC cell lines the sole tyrosine moiety present in CA IX's IC region can be phosphorylated via the EGFR pathway, which interacts with the p85 subunit of PI3K to activate Akt, which activation is implicated in cancer progression. That finding of that apparent third tumorigenic role for MN indicates that there is a positive feedback loop for CA9 expression in RCC, mediated by the PI3K pathway, which may contribute to the aggressiveness of RCC and potentially other preneoplastic/neoplastic diseases associated with abnormal MN/CA IX expression.

Preneoplastic/Neoplastic Tissues

The novel methods of the present invention concern treating preneoplastic/neoplastic diseases by preventing phosphorylation of CA IX's IC domain using EGFR pathway inhibitors, alone or in combination with MN-directed therapies. Those methods are expected to be effective for any preneoplastic/neoplastic disease characterized by abnormal MN/CA9 gene expression. Exemplary preneoplastic/neoplastic diseases include, among other preneoplastic/neoplastic diseases known to be associated with abnormal MN expression, at the least preneoplastic/neoplastic diseases selected from the group consisting of mammary, urinary tract, bladder, kidney, ovarian, uterine, cervical, endometrial, squamous cell, adenosquamous cell, vaginal, vulval, prostate, liver, lung, skin, thyroid, pancreatic, testicular, brain, head and neck, mesodermal, sarcomal, stomach, spleen, gastrointestinal, esophageal, colorectal and colon preneoplastic/neoplastic diseases.

As used herein, "cancerous" and "neoplastic" have equivalent meanings, and "precancerous" and "preneoplastic" have equivalent meanings.

MN Gene and Protein

The terms "CA IX" and "MN/CA9" are herein considered to be synonyms for MN. Also, the G250 antigen is considered to refer to MN protein/polypeptide [Jiang et al., *PNAS* (USA) 97: 1749-173 (2000)].

Zavada et al., WO 93/18152 and/or WO 95/34650 disclose the MN cDNA sequence shown herein in FIGS. 6A-6C [SEQ ID NO: 1], the MN amino acid sequence [SEQ ID NO: 2] also shown in FIGS. 6A-6C, and the MN genomic sequence [SEQ ID NO: 3]. The MN gene is organized into 11 exons and 10 introns.

The ORF of the MN cDNA shown in FIG. 6 has the coding capacity for a 459 amino acid protein with a calculated molecular weight of 49.7 kd. The overall amino acid composition of the MN protein is rather acidic, and predicted to have a pI of 4.3. Analysis of native MN protein from CGL3 cells by two-dimensional electrophoresis followed by immunoblotting has shown that in agreement with computer prediction, the MN is an acidic protein existing in several isoelectric forms with pIs ranging from 4.7 to 6.3.

The first thirty seven amino acids of the MN protein shown in FIGS. 6A-6C is the putative MN signal peptide [SEQ ID NO: 4]. The MN protein has an extracellular domain [amino acids (aa) 38-414 of FIGS. 6A-6C; SEQ ID NO: 5], a transmembrane domain [aa 415-434; SEQ ID NO: 6] and an intracellular domain [aa 435-459; SEQ ID NO: 7]. The extracellular domain contains the proteoglycan-like domain [aa 53-111: SEQ ID NO: 8] and the carbonic anhydrase (CA) domain [aa 135-391; SEQ ID NO: 9].

The CA domain is essential for induction of anchorage independence, whereas the TM anchor and IC tail are dispensable for that biological effect. The MN protein is also capable of causing plasma membrane ruffling in the transfected cells and appears to participate in their attachment to the solid support. The data evince the involvement of MN in the regulation of cell proliferation, adhesion and intercellular communication.

MN Gene—Cloning and Sequencing

FIG. 6A-C provides the nucleotide sequence for a full-length MN cDNA clone [SEQ ID NO: 1]. A complete MN genomic sequence is represented by SEQ ID NO: 3, and the nucleotide sequence for a proposed MN promoter is represented by SEQ ID NO: 24.

It is understood that because of the degeneracy of the genetic code, that is, that more than one codon will code for one amino acid [for example, the codons TTA, TTG, CTT, CTC, CTA and CTG each code for the amino acid leucine (leu)], that variations of the nucleotide sequences in, for example, SEQ ID NOS: 1 and 3 wherein one codon is substituted for another, would produce a substantially equivalent protein or polypeptide according to this invention. All such variations in the nucleotide sequences of the MN cDNA and complementary nucleic acid sequences are included within the scope of this invention.

It is further understood that the nucleotide sequences herein described and shown in FIG. 6 represent only the precise structures of the cDNA, genomic and promoter nucleotide sequences isolated and described herein. It is expected that slightly modified nucleotide sequences will be found or can be modified by techniques known in the art to code for substantially similar or homologous MN proteins and polypeptides, for example, those having similar epitopes, and such nucleotide sequences and proteins/polypeptides are considered to be equivalents for the purpose of this invention.

DNA or RNA having equivalent codons is considered within the scope of the invention, as are synthetic nucleic acid sequences that encode proteins/polypeptides homologous or substantially homologous to MN proteins/polypeptides, as well as those nucleic acid sequences that would hybridize to said exemplary sequences [SEQ. ID. NOS. 1, 3 and 24] under stringent conditions, or that, but for the degeneracy of the genetic code would hybridize to said cDNA nucleotide sequences under stringent hybridization conditions. Modifications and variations of nucleic acid sequences as indicated herein are considered to result in sequences that are substantially the same as the exemplary MN sequences and fragments thereof.

Only very closely related nt sequences having a homology of at least 80-90%, preferably at least 90%, would hybridize to each other under stringent conditions. A sequence comparison of the MN cDNA sequence shown in FIG. 6 and a corresponding cDNA of the human carbonic anhydrase II (CA II) showed that there are no stretches of identity between the two sequences that would be long enough to allow for a segment of the CA II cDNA sequence having 25 or more nucleotides to hybridize under stringent hybridization conditions to the MN cDNA or vice versa.

Stringent hybridization conditions are considered herein to conform to standard hybridization conditions understood in the art to be stringent. For example, it is generally understood that stringent conditions encompass relatively low salt and/or high temperature conditions, such as provided by 0.02 M to 0.15 M NaCl at temperatures of 50° C. to 70° C. Less stringent conditions, such as, 0.15 M to 0.9 M salt at temperatures ranging from 20° C. to 55° C. can be made more stringent by adding increasing amounts of formamide, which serves to destabilize hybrid duplexes as does increased temperature.

Exemplary stringent hybridization conditions are described in Sambrook et al., *Molecular Cloning: A Laboratory Manual*, pages 1.91 and 9.47-9.51 (Second Edition, Cold Spring Harbor Laboratory Press; Cold Spring Harbor, N.Y.; 1989); Maniatis et al., *Molecular Cloning: A Laboratory Manual*, pages 387-389 (Cold Spring Harbor Laboratory; Cold Spring Harbor, N.Y.; 1982); Tsuchiya et al., *Oral Surgery, Oral Medicine, Oral Pathology* 71(6): 721-725 (June 1991); and in U.S. Pat. No. 5,989,838, U.S. Pat. No. 5,972,353, U.S. Pat. No. 5,981,711, and U.S. Pat. No. 6,051,226.

Plasmids containing the MN genomic sequence (SEQ ID NO: 3)—the A4a clone and the XE1 and XE3 subclones—were deposited at the American Type Culture Collection (ATCC) on Jun. 6, 1995, respectively under ATCC Deposit Nos. 97199, 97200, and 97198.

MN Proteins and Polypeptides

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence shown in FIG. 6. Preferred MN proteins/polypeptides are those proteins and/or polypeptides that have substantial homology with the MN protein shown in FIG. 6. For example, such substantially homologous MN proteins/polypeptides are those that are reactive with the MN-specific antibodies, preferably the Mab M75 or its equivalent. The VU-M75 hybridoma that secretes the M75 Mab was deposited at the ATCC under HB 11128 on Sep. 17, 1992.

A "polypeptide" or "peptide" is a chain of amino acids covalently bound by peptide linkages and is herein considered to be composed of 50 or less amino acids. A "protein" is herein defined to be a polypeptide composed of more than 50 amino acids. The term polypeptide encompasses the terms peptide and oligopeptide.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

Preparation of MN-Specific Antibodies

The term "antibodies" is defined herein to include not only whole antibodies but also biologically active fragments of antibodies, preferably fragments containing the antigen binding regions. Further included in the definition of antibodies are bispecific antibodies that are specific for MN protein and to another tissue-specific antigen, preferably bispecific antibodies that are specific for MN protein and EGFR.

Antibodies useful according to the methods of the invention may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein includes polyclonal and monoclonal antibodies and biologically active fragments thereof including among other possibilities "univalent" antibodies [Glennie et al., *Nature*, 295: 715 (1982)]; Fab proteins including Fab' and F(ab)$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of the $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also oligonucleotide-directed mutagenesis techniques [Dalbadie-McFarland et al., *PNAS* (USA, 79: 6409 (1982)].

For many uses, particularly for pharmaceutical uses or for in vivo tracing, partially or more preferably fully humanized antibodies and/or biologically active antibody fragments may be found most particularly appropriate. Such humanized antibodies/antibody fragments can be prepared by methods well known in the art.

The antibodies useful according to this invention to identify MN proteins/polypeptides can be labeled in any conventional manner, for example, with enzymes such as horseradish peroxidase (HRP), fluorescent compounds, or with radioactive isotopes such as, $^{125}$I, among other labels. A preferred label, according to this invention is $^{125}$I, and a preferred method of labeling the antibodies is by using chloramine-T [Hunter, W. M., "Radioimmunoassay," *In: Handbook of Experimental Immunology*, pp. 14.1-14.40 (D. W. Weir ed.; Blackwell, Oxford/London/Edinburgh/Melbourne; 1978)]. Other exemplary labels may include, for example, allophycocyanin and phycoerythrin, among many other possibilities.

Representative monoclonal antibodies useful according to this invention include Mabs M75, MN9, MN12 and MN7 described in earlier Zavada et al. patents and patent applications. [U.S. Pat. No. 6,297,041; U.S. Pat. No. 6,204,370; U.S. Pat. No. 6,093,548; U.S. Pat. No. 6,051,226; U.S. Pat. No. 6,004,535; U.S. Pat. No. 5,989,838; U.S. Pat. No. 5,981,711; U.S. Pat. No. 5,972,353; U.S. Pat. No. 5,955,075; U.S. Pat. No. 5,387,676; US Application Nos: 20050031623, 20030049828, and 20020137910; and International Publication No. WO 03/100029]. Monoclonal antibodies useful according to this invention serve to identify MN proteins/polypeptides in various laboratory prognostic tests, for example, in clinical samples. For example, monoclonal antibody M75 (Mab M75) is produced by mouse lymphocytic hybridoma VU-M75, which was deposited under ATCC designation HB 11128 on Sep. 17, 1992 at the American Tissue Type Culture Collection [ATCC]. The production of hybridoma VU-M75 is described in Zavada et al., International Publication No. WO 93/18152. Mab M75 recognizes both the nonglycosylated GST-MN fusion protein and native MN protein as expressed in CGL3 cells equally well. The M75 Mab recognizes both native and denatured forms of the MN protein [Pastorekova et al., *Virology*, 187: 620-626 (1992)].

General texts describing additional molecular biological techniques useful herein, including the preparation of antibodies include Berger and Kimmel, *Guide to Molecular Cloning Techniques, Methods in Enzymology*, Vol. 152, Academic Press, Inc. (1987); Sambrook et al., *Molecular Cloning: A Laboratory Manual*, (Second Edition, Cold Spring Harbor Laboratory Press; Cold Spring Harbor, N.Y.; 1989) Vols. 1-3; *Current Protocols in Molecular Biology*, F. M. Ausabel et al. [Eds.], Current Protocols, a joint venture between Green Publishing Associates, Inc. and John Wiley & Sons, Inc. (supplemented through 2000); Harlow et al., *Monoclonal Antibodies: A Laboratory Manual*, Cold Spring Harbor Laboratory Press (1988), Paul [Ed.]; *Fundamental Immunology*, Lippincott Williams & Wilkins (1998); and Harlow et al., *Using Antibodies: A Laboratory Manual*, Cold Spring Harbor Laboratory Press (1998).

Epitopes

The affinity of a MAb to peptides containing an epitope depends on the context, e.g. on whether the peptide is a short sequence (4-6 aa), or whether such a short peptide is flanked by longer aa sequences on one or both sides, or whether in testing for an epitope, the peptides are in solution or immobilized on a surface. Therefore, it would be expected by ones of skill in the art that the representative epitopes described herein for the MN-specific MAbs would vary in the context of the use of those MAbs.

The term "corresponding to an epitope of an MN protein/polypeptide" will be understood to include the practical possibility that, in some instances, amino acid sequence variations of a naturally occurring protein or polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the protein or polypeptide containing them is immunogenic and antibodies elicited by such a polypeptide or protein cross-react with naturally occurring MN proteins and polypeptides to a sufficient extent to provide protective immunity and/or anti-tumorigenic activity when administered as a vaccine.

Immunodominant Epitopes in PG Domain and In Neighboring Regions

As indicated above, the extracellular domain of the full-length CA IX comprises the PG and CA domains as well as some spacer or perhaps hinge regions. The CA IX immunodominant epitopes are primarily in the PG region at about aa 53-111 (SEQ ID NO: 8) or at about aa 52-125 [SEQ ID NO: 31], preferably now considered to be at about aa 52-125 [SEQ ID NO: 31]. The immunodominant epitopes of CA IX may be located in regions neighboring the PG region. For example, the epitope for aa 36-51 (SEQ ID NO: 21) would be considered an immunodominant epitope.

The main CA IX immunodominant epitope is that for the M75 MAb. The M75 monoclonal antibody is considered to be directed to an immunodominant epitope in the N-terminal, proteoglycan-like (PG) region of CA IX. Alignment of amino acid sequences illustrates significant homology between the MN/CA IX protein PG region (aa 53-111) [SEQ ID NO: 8] and the human aggrecan (aa 781-839) [SEQ ID NO: 10]. The epitope of M75 has been identified as amino acid sequence PGEEDLP (SEQ ID NO: 11), which is 4× identically repeated in the N-terminal PG region of CA IX [Zavada et al. (2000)]. Closely related epitopes to which the M75 MAb may also bind, which are also exemplary of immunodominant epitopes include, for example, the immunodominant 6× tandem repeat that can be found at amino acids (aa) 61-96 (SEQ ID NO: 12) of FIG. 6A-6C, showing the predicted CA IX amino acid sequence. Variations of the immunodominant tandem repeat epitopes within the PG domain include GEEDLP (SEQ ID NO: 13) (aa 61-66, aa 79-84, aa 85-90 and aa 91-96), EEDL (SEQ ID NO: 14) (aa 62-65, aa 80-83, aa 86-89, aa 92-95), EEDLP (SEQ ID NO: 15) (aa 62-66, aa 80-84, aa 86-90, aa 92-96), EDLPSE (SEQ ID NO: 16) (aa 63-68), EEDLPSE (SEQ ID NO: 17) (aa 62-68), DLPGEE (SEQ ID NO: 18) (aa 82-87, aa 88-93), EEDLPS (SEQ ID NO: 19) (aa 62-67) and GEDDPL (SEQ ID NO: 20) (aa 55-60). Other immunodominant epitopes could include, for example, aa 68-91 (SEQ ID NO: 22).

The monoclonal antibodies MN9 and MN12 are considered to be directed to immunodominant epitopes within the N-terminal PG region SEQ ID NOS: 19-20, respectively. The MN7 monoclonal antibody could be directed to an immunodominant epitope neighboring the PG region at aa 127-147 (SEQ ID NO: 23) of FIG. 6A-6C.

An epitope considered to be preferred within the CA domain (SEQ ID NO: 9) is from about aa 279-291. An epitope considered to be preferred within the intracellular domain (IC domain) (SEQ ID NO: 7) is from about aa 435-450. An exemplary preferred MN-specific antibody that specifically binds the carbonic anhydrase domain of MN protein is the V/10 Mab, which is produced by the hybridoma VU-V/10, deposited at BCCM™/LMBP in Ghent, Belgium under Accession No. LMBP 6009CB.

Assays

Assays to Screen for MN/CA9 Gene Expression in Tissues

The methods may comprise screening for MN/CA9 gene expression product, if any, present in a sample taken from a patient diagnosed with preneoplastic/neoplastic disease; the MN/CA9 gene expression product can be MN protein, MN polypeptide, mRNA encoding a MN protein or polypeptide, a cDNA corresponding to an mRNA encoding a MN protein or polypeptide, or the like. If the MN/CA9 gene expression product is present at abnormal levels in said sample, the patient may be a suitable candidate for the therapeutic methods of the invention. In most cases, the abnormal levels would be increased MN/CA9 expression levels in tissues that do not normally express MN.

In a preferred embodiment of the invention, the MN gene expression product is MN antigen, and the presence or absence of MN antigen is screened in preneoplastic/neoplastic mammalian samples, preferably human samples. Such preneoplastic/neoplastic samples can be tissue specimens, tissue extracts, cells, cell lysates and cell extracts, among other samples. Preferred tissue samples are formalin-fixed, paraffin-embedded tissue samples or frozen tissue samples.

It can be appreciated by those of skill in the art that various other preneoplastic/neoplastic samples can be used to screen for the MN gene expression products. For example, in the case of a patient afflicted with a neoplastic disease, wherein the disease is a tumor, the sample may be taken from the tumor or from a metastatic lesion derived from the tumor.

It can further be appreciated that alternate methods, in addition to those disclosed herein, can be used to quantify the MN gene expression products.

In preferred embodiments, the gene expression product is MN antigen which is detected by immunohistochemical staining (e.g., using tissue arrays or the like). Preferred tissue specimens to assay by immunohistochemical staining, for example, include cell smears, histological sections from biopsied tissues or organs, and imprint preparations among other tissue samples. Such tissue specimens can be variously maintained, for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, percutaneous punch, and surface biopsies, among other biopsy techniques.

Many formats can be adapted for use with the methods of the present invention. The detection and quantitation of MN protein or MN polypeptide can be performed, for example, by Western blots, enxyme-linked immunosorbent assays, radioimmunoassays, competition immunoassays, dual antibody sandwich assays, immunohistochemical staining assays, agglutination assays, fluorescent immunoassays, immunoelectron and scanning microscopy using immunogold, among other assays commonly known in the art. The detection of MN gene expression products in such assays can be adapted by conventional methods known in the art.

It is also apparent to one skilled in the art of immunoassays that MN proteins or polypeptides can be used to detect and quantitate MN antigen in body tissues and/or cells of patients. In one such embodiment, an immunometric assay may be used in which a labelled antibody made to MN protein is used. In such an assay, the amount of labelled antibody which complexes with the antigen-bound antibody is directly proportional to the amount of MN antigen in the sample.

Methods of EGFR-Directed Cancer Therapy Based on Detection of Abnormal MN Expression EGFR Pathway Inhibitors As indicated above, the invention is based upon the discovery that the sole tyrosine moiety in the IC region of CA IX can be phosphorylated in an EGFR-dependent manner and result in activation of Akt, which activation is implicated in cancer progression. Therefore, EGFR pathway inhibitors can be used therapeutically to treat preneoplastic/neoplastic diseases characterized by abnormal MN/CA9 gene expression.

As used herein, "EGFR pathway inhibitors" include any therapies that are targeted to the EGFR pathway, including targeting any of the EGFR components. Preferred therapies that target the EGFR pathway include EGFR-specific antibodies, EGFR tyrosine kinase inhibitors, and other EGFR-targeted agents [recently reviewed in Marshall, *Cancer,* 107 (6): 1207-1218 (2006)].

Monoclonal antibodies (MAbs) block the extracellular ligand-binding portion of the EGFR and interfere with its activation. Exemplary EGFR pathway inhibitors that have been approved by the U.S. Food and Drug Administration include cetuximab (IMC-225, Erbitux™; ImClone Systems, Princeton, N.J.), a monoclonal antibody for the treatment of colorectal cancer. Other exemplary EGFR-specific Mabs that are undergoing clinical testing are panitumumab (ABX-EGF; Abgenix, Fremont, Calif.), nimotuzumab (TheraCIM™, h-R3; CIMYM Biosciences, Ontario, Canada), matuzumab (EMD-72000; EMD Pharmaceuticals/Merck KgaA); MDX-447, a dual EGFR and CD64 inhibitor (HuMax™-EGFr; Medarex, Princeton, N.J.), and Mab-806 (Ludwig Institute, Victoria, Australia).

In contrast, tyrosine kinase inhibitors (TKIs) block induction of the intracellular tyrosine kinase-mediated signaling pathways by binding at or near the ATP binding site on the intracellular kinase domain. Exemplary small-molecule EGFR TKIs that have received U.S. FDA approval are erlotinib (Tarceva®, OSI-774; CP-358,774; OSI Pharmaceuticals in collaboration with Genentech and Roche pharmaceuticals) for the treatment of NSCLC and pancreatic cancer, and gefitinib (Iressa®, ZD1839; AstraZeneca, Wilmington, Del.) for NSCLC. Cenertinib (CI-1033; Pfizer Pharmaceuticals, Groton, Conn.) is an irreversible, pan-ErbB inhibitor of receptor tyrosine kinase phosphorylation that has undergone Phase I studies. Additional exemplary TKIs that are in Phase I and/or Phase II clinical trials are the irreversible EGFR and HER-2 dual inhibitor EKB-569 (Wyeth-Ayerst, Madison, N.J.); and three dual-EGFR/ErbB-2-reversible EGFR TKIs, PKI-166 (Novartis International, BaseI, Switzerland), GW572016 (GlaxoSmithKline, Research Triangle Park, N.C.), and ARRY-334543 (Array BioPharma, CO). Still other TKIs currently in preclinical development are PD153035 and PD158780 (Parke-Davis, Ann Arbor, Mich.).

Use of EGFR Inhibitors with Conventional or MN-Directed Therapies

According to the methods of the invention, the EGFR inhibitors can be combined with MN/CA IX-specific antibodies and a variety of conventional therapeutic drugs, different inhibitors of cancer-related pathways, bioreductive drugs, and/or radiotherapy, wherein different combinations of treatment regimens with the EGFR inhibitors may increase overall treatment efficacy. Preferred therapies to be used in combination with EGFR inhibitors are inhibitors of the PI3K pathway and/or the MAPK pathway, as well as MN-directed therapies.

PI3K Pathway Inhibitors

Activation of the phosphotidylinositol-3-kinase (PI3K)/Akt cell survival pathway in many cancers, and its newly-discovered association with CA IX's IC domain, makes it an obvious target for cancer therapy. Because this pathway also has an important role in the survival of normal cells, however, it is important to achieve cancer selectivity; the cancer-selective proapoptotic protein Par-4 is a key target for inactivation by PI3K/Akt signaling [Goswami et al., *Cancer Res.,* 66(6): 2889-2892 (2006)]. Several anticancer therapies target, albeit indirectly, the PI3K/Akt pathway and cause inhibition of Akt1 phosphorylation and induction of apoptosis. Examples include Herceptin®, which inhibits ErbB-2 in breast cancer cells; cyclooxygenase-2 (COX-2) inhibitors, which inhibit COX-2 and PD1 in colon and prostate cancer; and imatinib mesylate (Gleevec, STI-571), which targets bcr-abl in leukemia.

MAPK Inhibitors

As used herein, "MAPK pathway inhibitors" include any therapies that are targeted to the MAPK pathway, including targeting any of the MAPK components, such as, Ras, Raf, MEK, and ERK, including but not limited to inhibition of their protein expression (e.g., antisense oligonucleotides), prevention of membrane localization essential for MAPK activation, and inhibition of downstream effectors of MAPK (e.g., Raf serine/threonine kinases) [for review of MAPK inhibitors, see Gollob et al., *Semin Oncol.,* 33(4): 392-406 (2006)]. MAPK pathway-directed therapies include but are not limited to multi-kinase inhibitors, tyrosine kinase inhibitors, monoclonal antibodies, as well as biologically active antibody fragments, polyclonal antibodies, and anti-anti-idiotype antibodies and related antibody based therapies, bis-aryl ureas, and omega-carboxypyridyl substituted ureas and the like. Preferred MAPK pathway inhibitors are Raf kinase inhibitors, which are described in more detail below Thus far, the most successful clinical drugs targeting the Ras/Raf/MEK/ERK cascade appear to be those that target Raf [Schreck and Rapp, *Int. J. Cancer,* 119: 2261-2271 (2006)], including the multi-kinase inhibitor Sorafenib (BAY 43-9006), and antisense and heat shock protein 90 (HSP90) inhibitors.

An exemplary and preferred MAPK pathway-directed therapy according to the invention is the bis-aryl urea Sorafenib (BAY 43-9006) [Nexavar®; Onyx Pharmaceuticals, Richmond, Calif. (USA), and Bayer Corporation, West Haven, Conn. (USA); Wilhelm and Chien, *Curr Pharm Des,* 8: 2255-2257 (2002); Wilhelm et al., *Cancer Res.,* 64: 7099-7109 (2004); Strumberg, D, *Drugs Today (Barc),* 41: 773-84, 2005; Lyons et al., *Endocrine-Related Cancer,* 8: 219-225 (2001)], a small molecule and novel dual-action inhibitor of both Raf (a protein-serine/threonine kinase) and VEGFR (vascular endothelial growth factor receptor, a receptor tyrosine kinase), and consequently an inhibitor of both tumor cell proliferation and angiogenesis. In addition, Sorafenib has been found to inhibit several other receptor tyrosine kinases involved in tumor progression and neovascularization, including PDGFR-β, Flt-3, and c-KIT. In December 2005 Sorafenib was approved by the FDA for patients with advanced renal cell carcinoma (RCC). Other preferred MAPK-directed therapies according to the invention are omega-carboxypyridyl substituted ureas, which are derivatives of bis-aryl ureas with improved solubility in water [Khire et al., *Bioorg Med Chem. Lett.*, 14(3): 783-786 (2004)].

Other exemplary therapies that target the MAPK pathway include MEK inhibitors. PD-0325901 (Pfizer) and ARRY-142886 (AZD-6244, Array and AstraZeneca) are small-molecule inhibitors currently in clinical development [Gollob et al., *Semin Oncol.*, 33(4): 392-406 (2006); Doyle et al., *Proc Am Soc Clin Oncol*, 24: 3075, 2005 (Abstr.); Lee et al., *Cancer* 2: 368 (2004) (Suppl.)] Those two orally available agents are non-ATP competitive allosteric inhibitors of MEK, which unlike the majority of ATP-competitive analogs, show high selectivity for MEK in biochemical assays. PD-0325901 is a second-generation compound derived from CI-1040 (PD184352, Pfizer), an oral MEK inhibitor which began Phase II clinical trials. PD-0325901 has an $IC_{50}$ value 200-fold lower than CI-1040, and is also more soluble with improved metabolic stability and bioavailability. PD-0325901 and ARRY-142886 have shown potent anti-tumor activity in tumor xenograft models. ARRY-142886 is currently being evaluated in phase 1 trials, while phase I/II clinical trial findings have recently been reported with PD-0325901.

MN-Directed Therapies

Because of MN protein's unique characteristics, it is an attractive candidate target for cancer therapy. In comparison to other tumor-related molecules (e.g. growth factors and their receptors), MN has the unique property of being differentially expressed in preneoplastic/neoplastic and normal tissues. Because of the extremely limited expression of MN protein in normal tissues, chemotherapeutic agents that target its expression would be expected to have reduced side effects, relative to agents that target proteins more extensively found in normal tissues (e.g., tamoxifen which binds the estrogen receptor, and finasteride which binds the androgen receptor). Furthermore, Phase I and II clinical trials of an MN-specific drug, Rencarex®, have shown that at least one MN-specific agent is well-tolerated, with no serious drug-related side effects, further supporting MN as a possible target for cancer chemotherapy.

Many MN-directed therapies may be useful according to the methods of the present invention, to be used in combination with EGFR pathway inhibitors to treat preneoplastic/neoplastic diseases associated with abnormal MN expression. Preferred therapies comprise therapies selected from the group consisting of MN-specific antibodies, MN-preferential carbonic anhydrase inhibitors, MN antisense nucleic acids, MN RNA interference, and MN gene therapy vectors; some of which preferred therapies are described in greater detail below.

Particularly, the EGFR specific inhibitors may be combined with therapy using MN/CA IX-specific antibodies and/or MN/CA IX-specific antibody fragments, preferably humanized MN/CA IX-specific antibodies and/or biologically active fragments thereof, and more preferably fully human MN/CA IX-specific antibodies and/or fully human MN/CA IX-specific biologically active antibody fragments. Said MN/CA IX-specific antibodies and biologically active MN/CA IX-specific antibody fragments, preferably human-ized and more preferably fully human, may be conjugated to the EGFR inhibitor, or to a cytotoxic entity, for example, a cytotoxic protein, such as ricin A, among many other cytotoxic entities.

MN-Preferential Carbonic Anhydrase Inhibitors

The novel methods of the present invention comprise inhibiting the growth of preneoplastic/neoplastic cells with compounds that preferentially inhibit the enzymatic activity of MN protein. Said compounds are organic or inorganic, preferably organic, more preferably sulfonamides. Still more preferably, said compounds are pyridinium derivatives of aromatic or heterocyclic sulfonamides. These preferred pyridinium derivatives of sulfonamides are likely to have fewer side effects than other compounds in three respects: they are small molecules, they are membrane-impermeant, and they are specific potent inhibitors of the enzymatic activity of the tumor-associated MN protein.

The pyridinium derivatives of sulfonamides useful according to the present invention can be formed, for example, by creating bonds between pyrylium salts and aromatic or heterocyclic sulfonamide reagents, as described in U.S. Patent Application No. 2004/0146955. The aromatic or heterocyclic sulfonamide portion of a pyridinium salt of a sulfonamide compound can be called the "head," and the pyridinium portion can be called the "tail."

It can be appreciated by those of skill in the art that various other MN-preferential carbonic anhydrase inhibitors can be useful according to the present invention.

MN Gene Therapy Vectors

Recent therapeutic strategies proposed to target aggressive tumors involve the utilization of the hypoxia-responsive promoters that can drive the expression of cytotoxic genes selectively in hypoxic tumor cells. This strategy requires that the promoter is turned on in the hypoxic conditions and turned off in the normoxic conditions. Several approaches are based on the use of repetitive hypoxia-responsive elements to achieve a higher magnitude of the hypoxic activation.

MN/CA9 is an excellent candidate for such hypoxia-regulated therapies in that it is one of the most tightly regulated by hypoxia genes, if not the most tightly regulated by hypoxia gene, found so far. However, even MN/CA9 displays some transcription activity under normoxia.

For inhibiting the expression of the MN gene using an oligonucleotide, it is possible to introduce the oligonucleotide into the targeted cell by use of gene therapy. The gene therapy can be performed by using a known method. For example, either a non-viral transfection, comprising administering the oligonucleotide directly by injection, or a transfection using a virus vector can be used, among other methods known to those of skill in the art. A preferred method for non-viral transfection comprises administering a phospholipid vesicle such as a liposome that contains the oligonucleotide, as well as a method comprising administering the oligonucleotide directly by injection. A preferred vector used for a transfection is a virus vector, more preferably a DNA virus vector such as a retrovirus vector, an adenovirus vector, an adeno-associated virus vector and a vaccinia virus vector, or a RNA virus vector.

Materials and Methods

Cell culture: SKRC-01, SKRC-08 and SKRC-17 RCC cell lines were a kind gift from Neil Bander (Weill Medical College, Cornell University, NY). Of these cells, the 01 and the 08 lines overexpressed CA IX protein whereas the SKRC-17 cell line did not. The cell lines were regularly maintained at 37° C. in a 95% air and 5% $CO_2$ incubator in Minimal Essential Medium (MEM) supplemented with 10% fetal bovine serum (FBS), 2 mM glutamine, 2 mM non-essential amino acids (NEAA), 50 IU/ml penicillin and 50 µg/ml streptomycin sulfate and 2.5 µg/ml fungizone. All reagent kits, recombinant proteins, antibodies and other reagents such as trypsin for replating the cells were used according to the manufacturer's recommendations.

EGF dependent phosphorvlation of CA IX: SKRC-01 cells, grown to 50% confluency in 60 mm culture dishes, were serum starved by growing them in serum-free medium supplemented with 0.1% FBS overnight. The medium was then changed to serum-free medium for a further 2 h. Recombinant EGF (rEGF, Santa Cruz) was dissolved in 10 mM acetic acid containing 0.1% BSA at a stock concentration of 50 µg/ml and increasing amounts of rEGF at final concentrations of 0-50 ng/ml were used to stimulate the serum starved cells for 30 min. Radioimmunoprecipitation assay buffer (RIPA) used in these studies consisted of 50 mM Tris-HCl pH 7.4, 150 mM NaCl, 1.0% NP-40, 0.5% sodium deoxycholate, 0.1% SDS containing the protease inhibitor cocktail (Roche Diagnostics) supplemented with 2 mM phenylmethyl sulfonyl fluoride (PMSF) and 1 mM activated sodium orthovanadate. Total RIPA lysates were prepared and equivalent amounts of RIPA lysates were processed for immunoprecipitation. Briefly, the RIPA lysates that have to be immunoprecipitated were treated with 20 µl of washed 50% suspension of protein A-agarose (Santa Cruz) for 30 min at 4° C. to eliminate non-specific protein binding. The beads were removed by centrifuging at 1000 g for 1 min and supernatants were retained. To the supernatants, a polyclonal antibody against CA IX (Santa Cruz) was added at 1:1000 dilution and subjected to gentle mixing in a rocker at 4° C. overnight. The immune complexes were collected by addition of 20 µl of 50% suspension of protein A-agarose. The samples were then rocked gently at 4° C. for 1 h. Immunoprecipitates were subjected to gel electrophoresis and blotted onto PVDF membranes. The blocked membranes were treated with a monoclonal antibody against phosphotyrosine (PY-20, Santa Cruz Biotechnology, CA) at 1:500 dilution. The membranes were washed and the blots were finally treated with goat anti-mouse immunoglobulin (IgG) conjugated to horse radish peroxidase (Santa Cruz at 1:3000 dilution). The signals were revealed with enhanced chemiluminescence. As a negative control, the initial immunoprecipitation was done by replacing the polyclonal antibody to CA IX with normal rabbit serum (Santa Cruz, 1:500 dilution) and following through the entire procedure. As a control for the amounts of protein loaded on each SDS-PAGE gel, the PVDF membranes with the transferred immune complexes from the polyclonal antibody (to CA IX) were probed with M75 monoclonal antibody to CA IX at a 1:1000 dilution (Bayer Corp, West Haven, Conn.), and the signals were visualized by enhanced chemiluminescence as described earlier. Parallel experiments were performed to determine the kinetics of the loss of tyrosine phosphorylation when the same SKRC-01 cells were serum starved and stimulated with 50 ng/ml EGF for 30 min as described earlier. The stimulus was then removed and the extent of phosphorylation was followed further for 90 min.

Preparation of lipid rafts from SKRC-01 cells: Lipid rafts were prepared from renal cancer cells according to the method of Goebel with few modifications [Goebel et al., Human Immunol. 63: 813-820 (2002)]. Briefly, around $4 \times 10^7$ cells were lysed in MES lysis buffer containing 25 mM MES (morpholinoethane sulfonic acid), 150 mM NaCl, 0.5% Triton X-100 and 2 mM EDTA for 30 min on ice and sonicated very briefly (3 one second pulses). An equal amount of 85% sucrose made in MES buffered saline (MBS) containing protease inhibitor cocktail at 1× concentration (Roche Diagnostics, Indianapolis, Ind.). Ultracentrifuge tubes were underlayed with 6 ml of 5% and 6 ml of 35% sucrose in MBS and finally the lysed cell suspension was underlayed with the help of a syringe and needle below the 35% sucrose layer. The tubes were spun at 104000 g at 4° C. for 20 h. The lipid rafts located at the interface of 5% and 35% sucrose layers were collected as 1 ml fractions. A 2 µl aliquot of the fractions was routinely spotted on to nitrocellulose membranes and processed with cholera toxin B-subunit conjugated with horse radish peroxidase (HRP) using the enhanced chemiluminescence method (ECL) to detect rafts.

Co-immunoprecipitation of PI3K with CA IX: Equal aliquots of the RIPA cellular extracts prepared from serum starved SKRC-01 cells and those prepared by stimulating the serum starved cells with 20 and 40 ng/ml EGF as described earlier were immunoprecipitated with M75 monoclonal antibody to CA IX (1:500 dilution) and the immune complexes were collected with Protein A/G Agarose (Santa Cruz). The denatured immune complexes were separated on 7.5% SDS-PAGE gels, transferred to PVDF membranes and blocked and probed with a polyclonal antibody to the p85 subunit of PI3K (Lab Vision, Freemont, Calif.). As a negative control, equivalent aliquots of the RIPA extracts used for the above experiment was separated on another gel and probed for the presence of the p85 subunit of PI3K using the same antibody as described above. In some cases, the lipid raft fraction isolated from the SKRC-01 cells that were serum starved and stimulated with 40 ng/ml EGF was also immunoprecipitated with M75 monoclonal antibody and probed for the co-immunoprecipitating PI3K (p85 subunit).

Phosphorylation status of Akt: To determine the activation of PI3K by interaction with the tyrosine phosphorylated carbonic anhydrase 1× protein, SKRC-17 cells which do not express CA IX protein were transiently transfected with vector only (pSG5C) or with wild-type CA IX cloned into pSG5C using the Transfast transfection kit (Promega Corporation, Madison, Wis.) exactly as described by Zatovicova and coworkers [Zatovicova et al., J Immunol Meth., 282: 117-134 (2003)]. The cells that underwent transfection were maintained in the $CO_2$ incubator for 64 h. At that time, the complete medium was replaced with a serum free medium supplemented with 0.1% FBS to mimic serum starvation conditions and the PI3K inhibitors LY 294002 and wortmannin were added at the indicated concentrations and the incubation continued for 8 more hours. Before completion of this experiment (i.e., at 72 h), the transfected cells in the presence or absence of the inhibitors were stimulated for 30 min in the presence of recombinant EGF (50 ng/ml). Whole cell extracts were made with the RIPA buffer and equivalent amounts of the extracts were analyzed on 7.5% denaturing polyacrylamide gels as described earlier. The transferred proteins on the PVDF membranes were probed with phosphospecific antibodies for Ser 473 or Thr 308 of Akt (1:1000 dilution, Akt sampler kit, Cell Signalling Technologies, Beverly, Mass.). Identical amounts of the extracts were run on another gel and probed with the antibody to unphosphorylated Akt (1:1000 dilution, Akt sampler kit, Cell Signalling Technologies, Beverly, Mass.) using the same blotting and probing conditions, as described above to verify that equivalent amounts of proteins in each sample had been analyzed.

Site directed mutagenesis of CA IX and stable transfection studies: The single tyrosine at position 449 of the wild-type CA IX protein was changed to phenylalanine using the Quick Change XL mutagenesis kit (Stratagene, La Jolla, Calif.) and the mutation (CA IX YF) was confirmed by subsequent sequencing [phosphorylation motif at aa 446-452 mutated to GVSFRPA (SEQ ID NO: 28)]. The "sense" (S) and the anti-sense (A) primers used for creating this mutation were synthesized from MWG-Biotech AG (Charlotte, N.C.). The S primer was 5'-CAA AGG GGG TGT GAG CTT CCG CCC AGC AGA GGT AG-3' [SEQ ID NO: 29] and the A primer was 5'-CTA CCT CTG CTG GGC GGA AGC TCA CAC CCC CTT TG-3' [SEQ ID NO: 30]. SKRC-17 cells constitutively expressing either wild-type CA IX or the CA IX YF mutant were obtained by co-transfection of the recombinant plasmids with the mammalian expression vector PcDNA 3.1 (neo) (Invitrogen, Carlsbad, Calif.) in a 10:1 ratio using the TransFast transfection kit (Promega Corp, Madison, Wis.) exactly according to the instructions by the manufacturer. The cells were selected for growth at a G418 concentration of 600 µg/ml and isolated with the use of cloning cylinders. The transfected clones were tested for CA IX expression and expanded further. Six individual cell populations were analyzed for CA IX expression to rule out the effect of clonal variation. As negative controls, the same SKRC-17 cells were transfected with empty vector pSG5C and PcDNA 3.1 and individual clones were selected for G418 resistance.

Analysis of HIF-1α in relation to CA IX expression and EGF stimulation: SKRC-01, 08 and 17 cells were serum starved as described earlier and stimulated with 50 ng/ml recombinant EGF. The same experiment was also performed with the SKRC-17 cells stably expressing the empty vector, wild-type CA IX plasmid and the CA IX YF mutant plasmid. RIPA lysates were prepared from all the cells at the end of each stimulation experiment. For SKRC-01, 08 and 17 lysates, equivalent proteins were separated on denaturing gels, immunoblots were prepared and probed for the presence of CA IX, Akt, phosho Akt (Ser 473), HIF-1α and HIF-1β. The polyclonal antibodies for HIF-1α and HIF-1β were purchased from Novus Biologicals, Littleton, Colo. The expression levels of total Akt and HIF-1β in these blots also served as a control amount of total protein separated on each gel. Immunoblots generated from the EGF stimulated and stably transfected lysates of SKRC-17 cells harboring the negative control, wild-type CA IX and the mutant CA IX were probed for the relative expression of Akt and the phosphorylated Akt (Ser 473) using the phospho-Akt pathway sampler kit as described above.

The following examples are for purposes of illustration only and are not meant to limit the invention in any way.

EXAMPLE 1

Intracellular Domain of CA IX can be Phosphorylated in an EGF Dependent Manner

Since epidermal growth factor receptor (EGFR) signaling is critically modulated by its localization in cholesterol rich membranes, and since its overexpression is well documented in the poor prognosis of renal cell carcinoma, the inventor investigated the effect of EGFR dependent signaling on the phosphorylation status of CA IX [Sun et al., *Biochemistry*, 41: 6338-6345 (2002); Dancey, J E, *J Clin Oncol* 22: 2975-2977 (2004)]. The results of these studies are shown in FIGS. 1A-C. The CA IX expressing SKRC-01 cells were serum starved and stimulated with increasing amounts of recombinant EGF and the RIPA extracts were made from these stimulated cells. These extracts were used in immunoprecipitation experiments with a polyclonal antibody to CA IX and the immune complexes collected were run on a denaturing polyacrylamide gel. The proteins transferred to PVDF membranes were probed for the presence of phosphotyrosine using a commercially available monoclonal antibody. This resulted in the visualization of the tyrosine phosphorylated version of CA IX as shown in FIG. 1, panel A. As a negative control, the same extracts were immunoprecipitated with a commercially available non-immune rabbit serum, processed the immune complexes collected and the resulting blots were probed with the same anti-phosphotyrosine antibody as described earlier which is shown in FIG. 1, panel B. The presence of equivalent amounts of CA IX used for all the lanes as a loading control are shown in FIG. 1, panel C after probing the blots with the M75 monoclonal antibody. These results indicate that CA IX is capable of receiving stimulatory signals from the epidermal growth factor receptor and participate in the ensuing signaling pathways. Since CA IX is also a very stable protein, the inventor investigated how this new CA IX function is regulated. The kinetics of loss of CA IX tyrosine phosphorylation is shown in FIG. 1D revealed a complete loss of signal after 75 min post stimulation.

EXAMPLE 2

Co-immunoprecipitation of Tyrosine Phosphorylated CA IX and p85 of PI3K

Some of the data from this study have indicated a functional cross-talk between CA IX and EGFR signaling pathways and suggests that the tyrosine phosphorylated version of CA IX could participate in the phosphatidyl inositol-3 Kinase (PI3K) signaling. To investigate this possibility, the inventor immunoprecipitated the serum starved and EGF stimulated extracts of SKRC-01 cells with the M75 monoclonal anti-CA IX antibody and probed the resulting blots for the possible association with PI3K. For this, a polyclonal antibody to the p85 subunit of the PI3K was used, which is shown in FIG. 2, upper panel. This figure shows that in the absence of any stimulatory signal, under completely serum starved conditions, there is no association of PI3K with the CA IX protein. This would be expected since the C-terminal Y is not phosphorylated under these conditions (lane 1). This figure also shows that there is an EGF concentration dependent increase in the amount of associated PI3K (lanes 2 and 3). In some experiments, the association of the tyrosine phosphorylated CA IX with PI3K was also verified in the membrane raft preparations made from the EGF stimulated SKRC-01 cells (upper panel, lane 4). This shows that CA IX is recruited to the lipid rafts where it could participate in signal transduction processes. To verify that equivalent amounts of proteins were loaded in the co-immunoprecipitation experiments, equivalent amounts of protein extracts were run on an independent gel and the resulting blot was probed for the presence of the p85 subunit of PI3K (lower panel). Based on these observations, the inventor infers that CA IX could be an active participant in the PI3K signaling pathways.

EXAMPLE 3

Activation of Akt by CA IX-pY and PI3K Interaction

Figure 3:
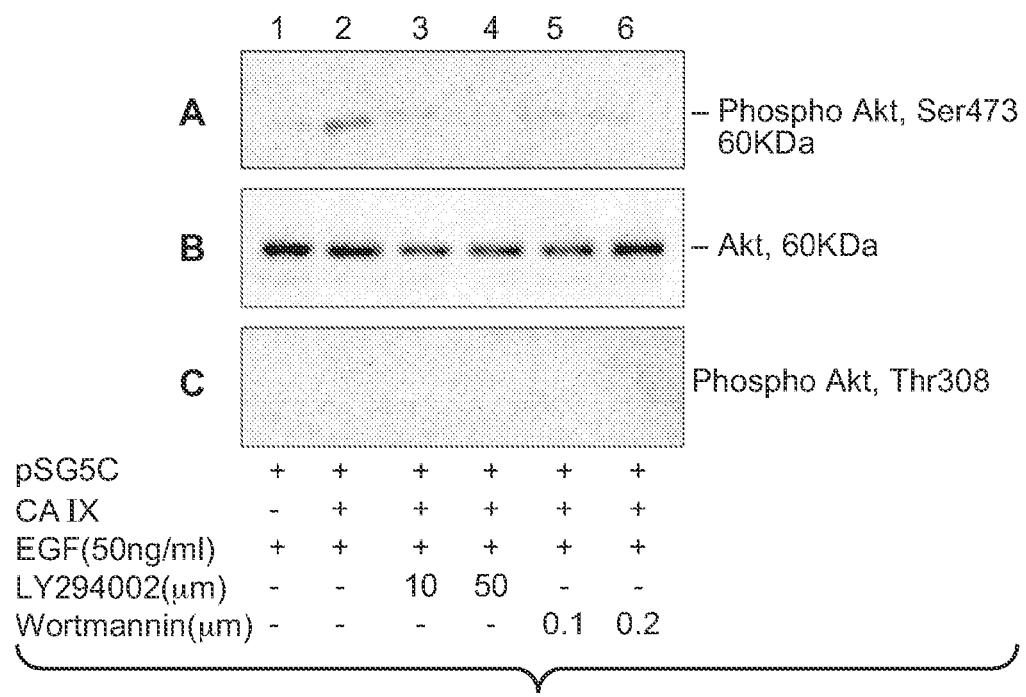
FIG. 3 shows the effect of pharmacological PI3K inhibition on the phosphorylation status of Akt. SKRC-17 cells (CA IX negative) were transiently transfected with the plasmid pSG5C-wtCAIX and serum starved before the start of the study. The cells were pretreated for 8 h with wortmannin and LY294002 at the indicated concentrations. At the end of this pretreatment period, the cells were stimulated with EGF and whole cell extracts were made with radioimmunoprecipitation (RIPA) buffer. Immunoblot assays were performed using antibodies against phosphorylated Akt (for serine 473 and threonine 308). As a measure of the loading controls, blots were probed for total unphosphorylated Akt protein, shown in panel B. Preliminary work with either vehicle only controls (DMSO) or EGF unstimulated controls showed no phosphorylation of either Ser 473 or Thr 308 in serum starved conditions (data not shown). Under the EGF stimulated conditions, the phosphorylation of Akt at Thr 308 was not observed (panel C).

The inventor then investigated whether the PI3K activation by association with CA IX could be reproduced in a CA IX negative RCC cell line such as SKRC-17 upon transfection with a wild-type CA IX plasmid and to investigate whether this associated PI3K could be pharmacologically blocked. The results of these studies are shown in FIG. 3. SKRC-17 cells were transiently transfected with either the wild-type CA IX containing plasmid or the vector alone and were treated with inhibitors in the presence or absence of recombinant EGF. Initial transfection experiments incorporating negative controls which included empty vector plasmid (pSG5C) in the absence of stimulating EGF (i.e., CA IX- and EGF-) showed no phosphorylation of either Ser 473 or Thr 308 of the Akt enzyme, the target of PI3K. It is well known that the activation of PI3K is triggered by the binding of its SH2 domain containing p85 regulatory subunit to phosphorylated tyrosine residues of activated growth factor receptors or their substrates [Vivanco I, and Sawyers C L. *Nat Rev Cancer,* 2: 489-501 (2002); Vanhaesebroeck et al., *Trends Biochem Sci.* 22: 267-272 (1997)]. Thus, in FIG. 3A in lane 2 from left, there is a significant increase in the Ser 473 phosphorylation of Akt under EGF stimulated conditions as studied by using a phospho-specific antibody for this species, upon transient transfection of CA IX, when compared to a relatively decreased phosphorylation level of the same protein in the absence of transfected CA IX but in the presence of EGF (FIG. 3A, lane 1). This implies that the activation of PI3K and subsequent phosphorylation of Ser 473 on Akt by EGF stimulation of CA IX expressing cells could be additive and could act as a synergistic mechanism in the activation of PI3K. These inferences could have significant implications with respect to therapeutic interference. Akt phosphorylation could be pharmacologically reduced by PI3K inhibitors, namely LY294002 and wortmannin (FIG. 3A, lanes 3-6 from left). At the indicated concentrations, LY294002 is shown to be a better inhibitor of both the base level and the CA IX stimulated PI3K activity when the phosphorylation status of Akt Ser 473 is studied. As other negative controls, the use of equivalent amounts of the vehicle dimethylsulfoxide (DMSO) that was used to dissolve these inhibitors did not have any effect on the PI3K activity (data not shown). As loading controls, equivalent amounts of protein extracts were run on another gel and probed for the presence of unphosphorylated Akt as a measure of total Akt, which is shown in FIG. 3B. However, no phosphorylation of threonine 308 of Akt was evident in these transfection studies (FIG. 3C). Nevertheless, these studies led the inventor to conclude that the introduction of the membrane bound CA IX in these CA IX negative RCC cells led to an additive activation of PI3K and subsequent activation of Akt under conditions of EGF stimulation.

EXAMPLE 4

Figure 4A:
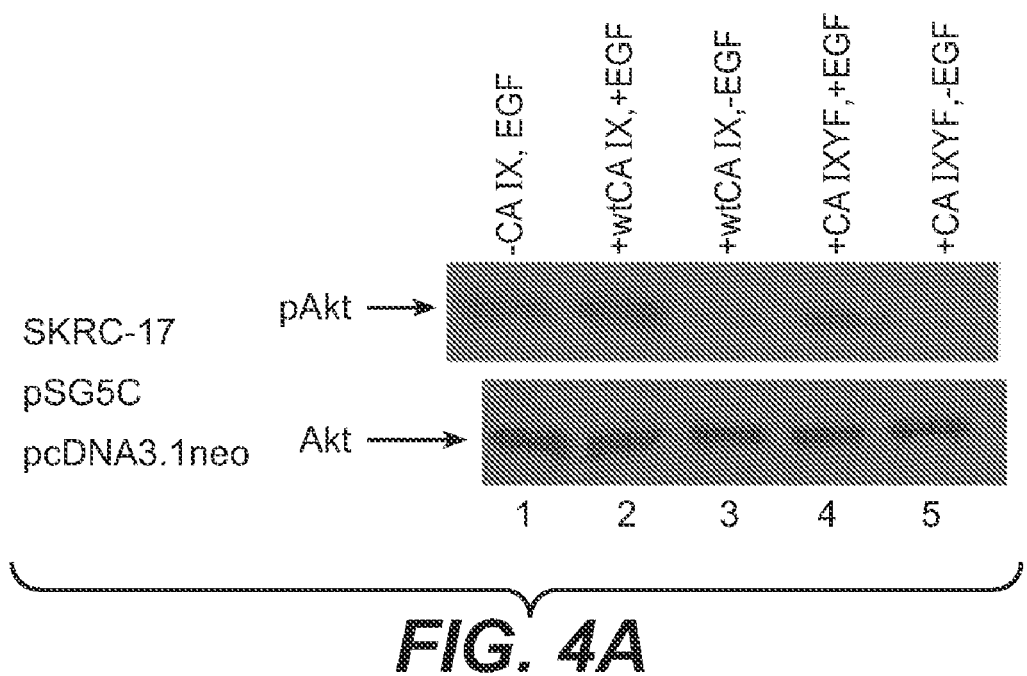
FIG. 4A depicts the effect of serum starvation and EGF stimulation in stably transfected SKRC-17 cells expressing CA IX as seen by the differences in Akt phosphorylation. Upper panel: immunoblot using the phosphospecific Akt (Ser 473) antibody as probe; Lower panel, an identical blot using antibody for the unphosphorylated Akt protein as probe, which also serves as a loading control. Lane 1: SKRC-17 cells transfected with empty vector pSG5C and pcDNA3.1 in the presence of EGF (50 ng/ml); lane 2: cells expressing wt CA IX in the presence of EGF; lane 3: G418 resistant cells expressing the wild-type CA IX in the absence of EGF (i.e., serum starvation); lane 4: CA IX YF mutant expressing cells in the presence of EGF and lane 5: CA IX YF mutant expressing cells in the absence of EGF.
Figure 4B:
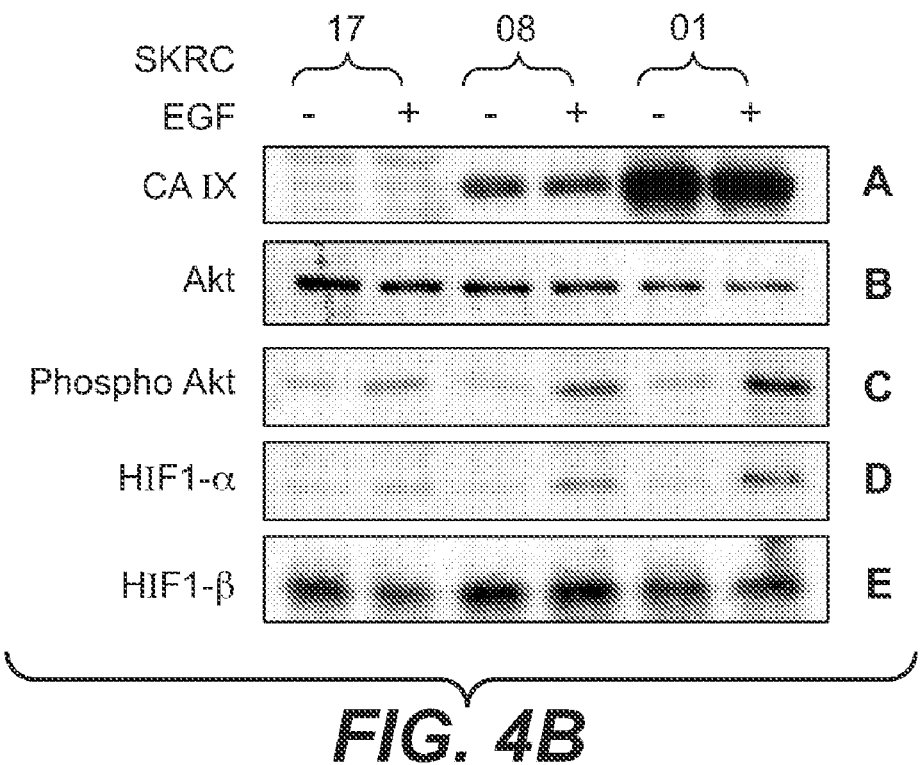
FIG. 4B shows the correlation of Akt phosphorylation with the level of expression of CA IX and HIF-1 protein subunits under normoxic conditions in SKRC cells. SKRC-17 (CA IX negative), −08 (low expression of CA IX) and −01 cells (high expression of CA IX) were serum starved and stimulated with 50 ng/ml EGF as described earlier. Thirty minutes post stimulus, cell lysates were prepared, subjected to denaturing gel electrophoresis and immunoblots were probed for the expression of CA IX (panel A), total unphosphorylated Akt (panel B), phosphoAkt (Ser473, panel C), HIF-1α subunit (panel D) and HIF-1β subunit (panel E) using specific antibodies. The signals were developed using the corresponding secondary antibodies conjugated with horse radish peroxidase (HRP) and enhanced chemiluminescence (ECL). Panels B and E also served as loading controls.

CA IX when Stably Transfected, Shows Elevated Akt Phosphorylation Under EGF Stimulated Conditions Since the above studies were done under conditions of transient transfection, that may or may not reflect physiological conditions, the inventor next investigated whether the phenomenon of Akt phosphorylation could be seen in SKRC-17 cells (which are CA IX negative) when they are transfected to express the human CA IX protein in a constitutive manner. For this purpose, the pSG5C-CA IX plasmid was co-transfected with pcDNA3.1-neo plasmid at the same ratio as described by Svastova and G418 resistant cells were selected [Zatovicova et al., *J Immunol Meth.,* 282: 117-134 (2003); Svastova et al., *FEBS Lett.,* 577: 439-445 (2004)]. In parallel, SKRC-17 cells stably expressing the CA IX YF mutant protein was also selected under identical conditions. As negative controls for these stable transfection experiments, SKRC-17 cells expressing empty vectors pSG5C and pcDNA3.1-neo were also selected. The cells were serum starved and stimulated with 50 ng/ml recombinant EGF as described earlier. RIPA lysates prepared from these cells were subjected to denaturing gel electrophoresis and immunoblots were probed for the expression of total and phosphorylated Akt (Ser 473) proteins. The results of a typical experiment are shown in FIG. 4A. While the total Akt amount that was followed in each experimental condition was equivalent, the differences in the level of Akt phosphorylation was more significant in wild-type CA IX expressing SKRC17 cells with higher Akt phosphorylation (FIG. 4A, lane 2) compared to the same cells without CA IX expression, both in the presence of EGF (FIG. 4A, lane 1). Whereas, when the same cells expressed the YF mutant of CA IX, significantly less phosphorylated Akt (FIG. 4A, lane 4) was detected. The corresponding negative controls for these CA IX proteins in the absence of EGF (serum starvation) showed basal levels of Akt phosphorylation (FIG. 4A, lanes 3 and 5). These results suggest that among other factors such as EGF/EGFR induced phosphorylation of Akt, CA IX phosphorylation may be another important factor contributing to the phosphorylation/activation status of Akt and that the mutation of this single tyrosine to phenylalanine in the intracellular domain of CA IX abrogates this Akt activating function of CA IX. Finally, the inventor investigated whether the extent of Akt phosphorylation can be correlated with the level of CA IX expression in cells naturally overexpressing CA IX, and whether the relative increase in the extent of Akt phosphorylation can be translated to an increase in the expression of HIF-1α levels in these SKRC cells that inherently differ in their levels of CA IX expression. For these experiments, the same SKRC-01 and 08 cells which are CA IX positive and SKRC-17 cells which are CA IX negative were chosen and the results are shown in FIG. 4B. These cells were serum starved and stimulated with 50 ng/ml recombinant EGF as described earlier, and the relative levels of expression of CA IX (panel A), total Akt (panel B), phosphorylated Akt (panel C), HIF-1α (panel D) and HIF-1β (ARNT protein, panel E) were followed by immunoblotting with specific antibodies. The results presented in FIG. 4B essentially reinforce the concept that in CA IX overexpressing cells, growth factor stimulation results in a relative increase in Akt phosphorylation and an increase in the expression level of HIF-1α, whereas the expression level of HIF-1β is unchanged. Since all these experiments were done under normoxic conditions, these results will have important implications for hypoxia dependent and independent modes HIF-1α expression in the hypoxic core and tumor periphery where elevated CA IX expression could be seen [Potter and Harris, *Brit J Cancer,* 89: 2-7 (2003)].

Discussion

Even though CA IX expression is widely accepted as a marker of hypoxic regions in tumors, there are increasing number of studies which suggest that CA IX expression is regulated at multiple levels. Parallel studies that have focused on the expression of CA IX and pimonidazole staining for hypoxic regions revealed a non-overlapping pattern of expression of CA IX with hypoxic regions with the CA IX positive areas extending beyond regions of hypoxia [Beasley et al., *Cancer Res.,* 61: 5262-5267 (2001); Olive et al., *Cancer Res.,* 61: 8924-8929 (2001)]. Varying amounts of HIF-1α can be detected at mildly hypoxic and even under normoxic conditions in normal tissues and in cell lines [Richard et al., *J Biol Chem.,* 275: 26765-26771 (2000)]. CA IX expression was also found to be regulated by cell density [Kaluz et al., *Cancer Res.,* 62: 4469-4477 (2002)]. Its expression is very low in sparse and rapidly proliferating HeLa cell cultures whereas its synthesis is induced in dense cultures, very likely triggered by intermediate oxygen tensions or transient hypoxia. This process has recently been shown to involve the activation of the PI3K pathway [Kaluz et al., *Cancer Res.*, 62: 4469-4477 (2002)]. Apart from this, CA IX was also expressed in necrotic regions which are known to be hypoxic [Leek et al., *Brit J Cancer*, 79: 991-995 (1999)]. But in these necrotic and perinecrotic regions, other mechanisms such as the production of TNF-α, the reactive oxygen species (ROS) and NF-kB plays a role in the production of HIF-1α which in turn induces the expression of its target gene, namely CA IX [Haddad and Land, *FEBS Lett.*, 505: 269-274 (2001)]. This is more so in non-clear cell carcinomas of the kidney such as the papillary type 1 tumors, whereas in clear cell carcinomas with VHL gene inactivation either in an inherited manner or in a sporadic manner, there is a near uniform expression of CA IX throughout the tumor [Leek et al., *Brit J Cancer*, 79: 991-995 (1999) and Wykoff et al., *Cancer Res*, 60: 7075-7083 (2000)]. Thus, the multiple levels of regulation of expression of CA IX can be visualized as follows: (1) factors such as frank hypoxia in the core of the tumor or VHL gene mutations in clear cell RCC tumors that force HIF1α stabilization; (2) pericellular hypoxic or mildly hypoxic regions which are not hypoxic enough to induce HIF-1α stabilization but induce CA IX at intermediate HIF-Iα levels through the participation of the PI3K pathway; (3) regions where necrotic foci are observed where the expression of HIF-1α can be supplemented by the expression of factors unique to necrotic foci such as TNF-α, ROS and NF-kB; and (4) regions of the tumor which are well supplied by oxygen where the expression of HIF-1α can be induced under normoxic conditions through mechanisms such as the overexpression of several growth factor receptors. Several clinical studies show a clear relationship between high levels of CA IX expression in tumors and poor prognosis [Loncaster et al., *Cancer Res*, 61: 6394-6399 (2001); Chia et al., *J Clin Oncol.* 19: 3660-3668 (2001); and Giatromalonaki et al., *Cancer Res*, 61: 7992-7998 (2001)].

Clear cell RCCs as well as papillary RCCs exhibit a complex and heterogeneous expression of several growth factors and their receptors, of which the role played by the epidermal growth factor receptor appears to be very significant [Moch et al., *Human Pathol*, 28: 1255-1259 (1997); and Uhlman et al., *Clin Cancer Res*, 1: 913-920 (1995)]. They are almost invariably characterized by an overexpression of EGFR and the cognate ligand TGF-α. Several studies indicated the functional intactness of the stimulatory autocrine loop for this receptor which contributes to cancer development and progression, including cell proliferation, suppression of apoptosis, angiogenesis and the metastatic spread [Ramp et al., *J Urol* 157: 2345-2350 (1997)]. Several recent studies have shown that this EGFR can mediate several signaling pathways on the basis of its residence in the cholesterol rich microdomains of the cancer cell [Goebel et al., *Human Immunol*, 63: 813-820 (2002); and Nanjundan et al., *J Biol Chem*, 278: 37413-37418 (2003)]. Modulation of cholesterol levels in these microdomains has been shown to alter the EGFR function and trafficking and even contribute to its ligand-independent activation [Chen X., and Resh M. D., *J Biol Chem*, 277: 49631-49637 (2002)]. These observations suggest that EGFR signaling from its location in the lipid rafts may have significant clinical implications and prompted us to test the possibility that CA IX could be phosphorylated by this receptor in a ligand-dependent manner. The inventor has found that this was indeed so in vitro. Upon ligand binding, the cytoplasmic tail of the EGFR gets autophosphorylated and this process helps in the activation of the tyrosine kinase activity of the receptor. In addition, the P-Tyr residues in the activated receptor also act as docking sites to cytoplasmic signal transducing adapter molecules that contain the SH2 or the phosphotyrosine binding (PTB) motifs [Schlessinger J., *Cell* 103: 211-225 (2000); and Yarden, Y. and Sliwkowski, M. Y., *Nat Rev Mol Cell Biol.* 2: 127-137 (2001)]. For the P-Tyr of CA IX, which is not endowed with any tyrosine kinase (TK) activity it may simply serve as a docking site for the same or a different set of signal transducing adapter molecules. Hence, its localization at the lipid raft regions may offer CA IX with a unique opportunity to recruit and direct a signaling pathway which is similar or different to that orchestrated by the EGFR. Thus, CA IX may play a role in amplifying or diversifying the oncogenic signaling processes elicited by the EGFR alone in renal cell carcinoma. In this context, knowledge of the complete spectrum of the signal transducing adapter molecules with which the tyrosine phosphorylated CA IX can interact becomes absolutely essential. This would offer unique opportunities to interfere with these signaling processes which may have significant therapeutic potential. Inhibition of multiple pathways such as CA IX phosphorylation, HIF-1α targeted therapies, VEGF-R targeted therapies and EGFR targeted therapies (as opposed to monotherapy using the EGFR antagonists only) would theoretically create an environment in the RCC cell that closely approximates to a restored pVHL function in clear cell carcinoma, even though in reality, there is a biallelic loss of this tumor suppressor gene or function. Thus, signal transduction therapeutics that involves several of these pathways will offer new avenues for therapeutic approach for RCC and may possibly synergize with existing therapies such as those with IL-2 and interferon-α.

The results also implicate the involvement of transmembrane carbonic anhydrase IX in PI3K pathway and suggest that CA IX, PI3K and EGFR signaling may function in an integrated manner to provide a molecular basis for the up-regulation of HIF-1α under non-hypoxic conditions in this cancer. Observations by Kaluz and coworkers [Kaluz et al., *Cancer Res*, 62: 4469-4477 (2002)] previously indicated a requirement for PI3K activity for the cell density dependent CA IX expression which might provide a link between the cancer-restricted expression of CA IX with the well established role of the PI3K pathway in tumorigenesis. The results reported in this study imply that the expression of CA IX and its signaling through the EGFR pathway would activate the PI3K pathway. This in effect would form the basis for a self-promoting signaling loop which might be a poor prognostic factor for clear cell RCC. This would also help in explaining why several tumors that have deregulated PI3K activity also have elevated expression of CA IX [Kaluz et al., *Cancer Res*, 62: 4469-4477 (2002)].

Several novel features of Akt activation process need to be highlighted here. The motif in the intracellular portion of CA IX protein ( . . . GVSYRPA . . . ) [SEQ ID NO: 25], and the consensus motif found by comparison with the corresponding region in CA XII ( . . . GVXYXPA) [SEQ ID NO: 26], do not conform to the canonical YXXM motif [SEQ ID NO: 27] preferred by the SH2 domain of class IA PI3K adapter p85 subunit. The reason for this is still not clear and it certainly warrants further studies. There could be several explanations for this observation which might be an exception to the rule. First, since occupation of both SH2 domains of the p85 subunit, preferably by two adjacent phosphotyrosine motifs of the binding protein is necessary for full activation of PI3K, the binding of the GVXYXPA motif to PI3K p85 subunit as seen in this study very likely brings up a relatively weaker activation of the PI3K enzyme as it may bind to the p85 subunit with a lower affinity [Rordorf-Nikolic et al., *J Biol Chem*, 270: 3662-3666 (1995)]. Second, it may also be possible that the GVXYXPA motif in CA IX protein interacts with another signal transducing adapter which in turn interacts with the p85 subunit of PI3K. Third, a non-canonical interaction of the p85 subunit with other proteins such as HGF/SCF (hepatocyte growth factor/scatter factor) receptor and ErbB3-p85 subunit was reported earlier, which may influence endocytic sorting and internalization [Hellyer et al., *Biochem J*, 333: 757-763 (1998); Ponzetto et al., *Mol Cell Biol*, 13: 4600-4608 (1993); and Wu et al., *J Biol Chem*, 278: 40425-40428 (2003)]. Finally, since CA IX is a very stable protein, unlike many other growth factor receptor proteins or signal transducing adapter proteins that undergo tyrosine phosphorylation, the observation that CA IX protein undergoes tyrosine phosphorylation in the first place is unique, and the physiological significance of this observation may extend well beyond its role in PI3K activation. In this respect, the full spectrum of all the binding partners of phosphorylated CA IX needs to be characterized.

Figure 5:
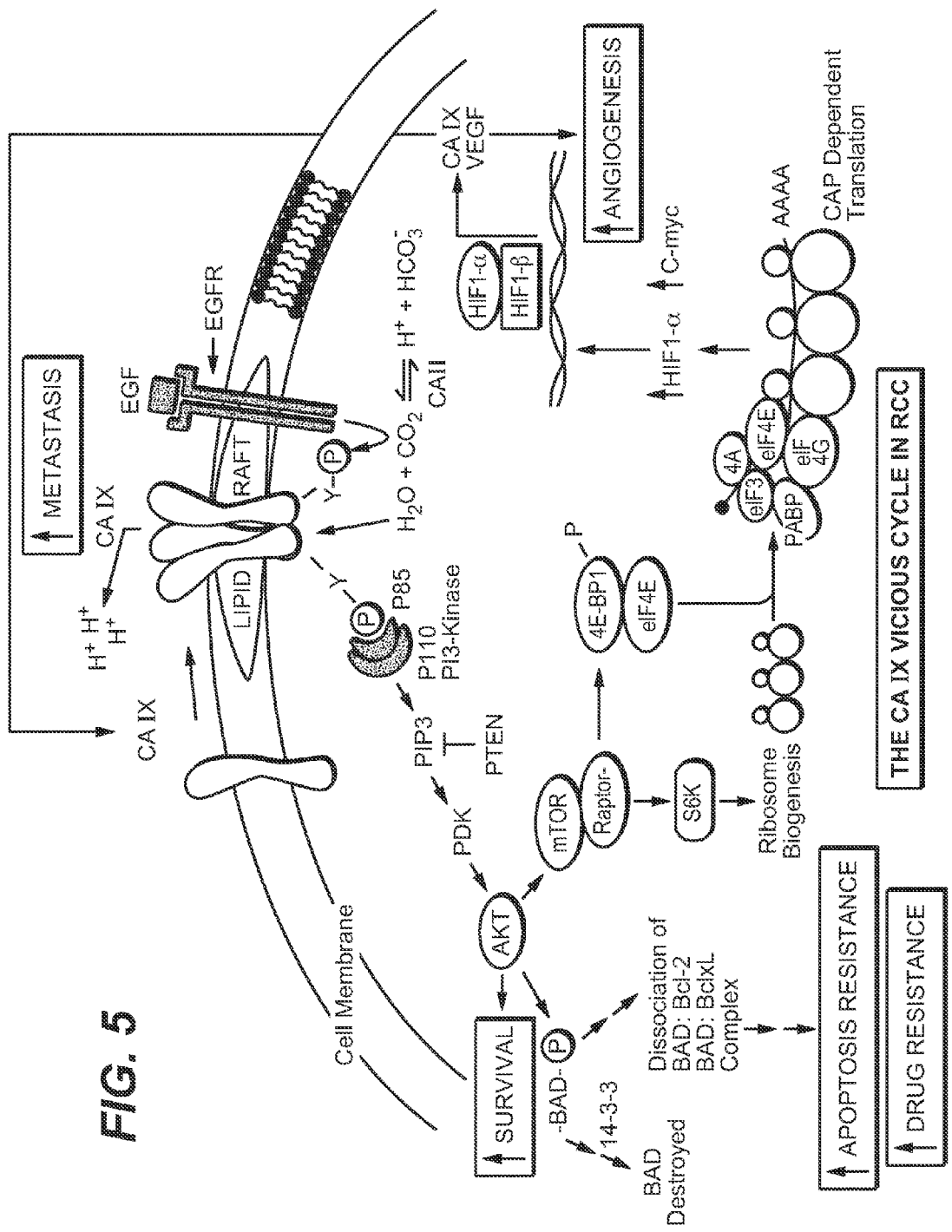
FIG. 5 provides a diagrammatic sketch of the major signaling pathways in clear cell carcinoma cell placing CA IX in the lipid rafts where it can get phosphorylated in a growth factor dependent manner and participate in the signaling processes regulated by PI3K and mammalian target of rapamycin (mTOR). The CA IX protein recruited to the lipid rafts is depicted in its dimerized form. This figure also depicts the established role of PI3K as a mediator of several survival, proliferation and apoptosis resistance pathways that lead to resistance to chemotherapeutic drugs. The major role of mTOR as an integrator of several signaling inputs is also presented with particular reference to cap-dependent translation of target proteins that include cyclin D1, c-myc and most importantly, HIF-1α. The placement of CA IX tyrosine phosphorylation in the midst of these cell signaling systems forms the basis of a vicious cycle, whereby CA IX mediated activation of Akt promotes the expression of HIF-Iα which in turn promotes the expression of CA IX leading to poor prognosis in advanced cases of clear cell RCC. Increased acidification of the extracellular compartment contributes to increased invasive potential. The HIF-α target gene VEGF contributes to enhanced angiogenesis which is one of the hallmarks of clear cell RCC.
Figure 7:
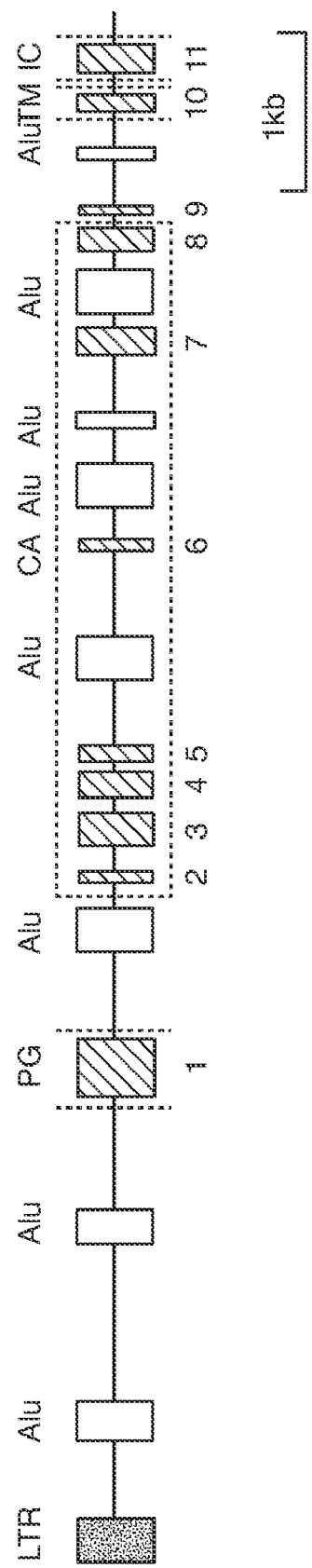
FIG. 7 provides an exon-intron map of the human MN/CA IX gene. The positions and sizes of the exons (numbered, cross-hatched boxes), Alu repeat elements (open boxes) and an LTR-related sequence (first unnumbered stippled box) are adjusted to the indicated scale. The exons corresponding to individual MN/CA IX protein domains are enclosed in dashed frames designated PG (proteoglycan-like domain), CA (carbonic anhydrase domain), TM (transmembrane anchor) and IC (intracytoplasmic tail).

One of the most important functions of the activated Akt protein is to activate the mammalian target of rapamycin (mTOR) as shown by numerous studies [Sekulic A., *Cancer Res*, 60: 3504-3513 (2000); Kozma S. C., and Thomas G., *BioEssays*, 24: 65-71 (2002); Vogt P. K., *Trends Mol Med*, 7: 482-484 (2001); and Aoki et al., *Proc Natl Acad Sci* (USA), 98: 136-141 (2001)]. The mTOR protein has been shown to be central homeostatic sensor receiving signals from a plethora of agents such as growth factors, amino acids, nutrients, intracellular ATP levels, oxygen levels, second messengers to integrate and coordinate the levels of ribosome biogenesis, cell cycle progression and translation initiation. Numerous pharmacological and genetic studies place the PI3K activation process upstream of the mTOR pathway [Bjornsti M. A., and Houghton P. J., *Nat Rev Cancer*, 4: 335-348 (2004); and Abraham R. T., *Cell* 111: 9-12 (2002)]. Among the many important functions of the activated mTOR protein, the most relevant for these studies is its ability to control the cap-dependent translation of certain mRNAs that have unique 50-untranslated region secondary structure such as in cyclin D1 and c-myc mRNAs which help in the unrestricted progression from GI to S phase of the cell cycle. Most notably, the HIF-1α protein is also synthesized in this manner [Page et al., *J Biol Chem*, 277: 48403-48409 (2002)]. In most cancers where the PI3K pathway is deregulated, the up-regulated mTOR can contribute to hypoxia independent translation of HIF-1α [Hudson et al., *Mol Cell Biol*, 22: 7004-7014 (2002); and Philips et al., *J Biol Chem*, 280: 22473-22481 (2005)]. But, in the case of renal cell carcinoma, with the loss of function of the VHL gene commonly seen in the clear cell type, there is net accumulation of this hypoxia driven transcription factor due to protein stabilization [Linehan, W. M., and Zbar, B., *Cancer Cell*, 6: 223-228 (2004); and Bjornsti M. A., and Houghton P. J., *Nat Rev Cancer*, 4: 335-348 (2004)]. This leads to the increased expression of (apart from CA IX) its growth factor target genes such as TGF-α, VEGF and PDGF. These growth factors in turn contribute in activating the mTOR pathway. Thus, in the clear cell RCC, mTOR can be up-regulated both by hypoxia driven as well as hypoxia independent pathways and those results place CA IX in the activation process of Akt in such a way that it may actually integrate both these HIF-1α dependent and independent pathways as shown in FIG. 5. The results also provide a molecular basis of the positive feed back loops that are inherent in such integrated pathways and help in the visualization of a vicious cycle mediated by CA IX mediated signaling. In particular, the scheme put together in FIG. 5 helps in placing the many functions of VHL protein and its relationship to the CA IX mediated signaling in proper perspective. It also represents a working hypothesis for the significance of over-expression of CA IX in clear cell carcinoma of the kidney. For example: (1) the VHL protein has been shown to down-regulate the expression and transport activity of certain anion exchangers (AE) which are in complex with CA II or the membrane associated CA IV that facilitates bicarbonate transport [Sterling et al., *J Biol Chem*, 277: 25239-25246 (2002)]. This suggests that the transmembrane CA IX could also function in a complex in a similar fashion as other carbonic anhydrases; (2) VHL tumor suppressor protein is the main regulator for the expression of HIF-1α causing a down-regulation of CA IX expression [Ivanov et al., *Proc Natl Acad Sci* (USA), 95: 12596-12601 (1998)]; (3) as a component of the hypoxic and non-hypoxic acidification machinery, CA IX might participate in pH dependent mechanism of nucleolar sequestration of VHL protein [Mekhail et al., *Nat Cell Biol*, 6: 642-647 (2004)]. Thus, enhanced acidification of the extracellular environment may produce a feed back loop of a down-regulated VHL environment which might lead to HIF-1α stabilization; (4) pVHL protein has also been shown to be required for efficient blockade of the epidermal growth factor receptor and the autocrine loops that are established in RCC [Perera et al., *Clin Cancer Res*, 6: 1518-1523 (2000)]; (5) moreover, expression of wild-type VHL in cells expressing a mutated endogenous VHL leads to decreased expression of TGF-α. TGF-α is a direct target for the VHL tumor suppressor which acts by decreasing the stability of TGF-α mRNA [Knebelmann et al., *Cancer Res*, 58: 226-231 (1998)]. Thus, by facilitating both the EGFR blockade and targeting the TGF-α mediated autocrine loop, the wild-type VHL protein can down regulate the vicious cycle of CA IX mediated cell signaling as put forward in this study; and (6) in addition, wild-type pVHL binds to and inactivates certain atypical protein kinase C family members such as PKC zeta and delta [Pal et al., *J Biol Chem*, 272: 27509-27512 (1997)]. In this regard, it is very interesting to note that some recent studies have implicated PKC β II as the PDK II kinase that can activate Akt at serine-473 [Kawakami et al., *J Biol Chem*, 279: 47720-47725 (2004)]. Thus, it would be logical to expect that pVHL would try to impede the Akt activation process which would in turn activate mTOR pathway as a consequence. Thus, all the phenomena described here go on to characterize the molecular signatures for the progression of clear cell carcinoma of the kidney and obviously, VHL inactivation serves the best interests of the cancer cell. Placement of CA IX as an active participant in the middle of these signaling pathways as shown by the studies reported here may further help in the understanding of the role of VHL and its relationship to the overexpression of CA IX in these processes and justify the therapeutic interference of these pathways. Finally, it is entirely possible that when the enzymatic activity is down-regulated by the use of specific CA IX inhibitors, the CA IX protein could still function in its signal transduction capacity. This warrants more investigations that focus on inhibiting CA IX in both its capacities to arrive at maximum therapeutic benefit. The patient's VHL and PTEN status will also determine the ultimate efficacy of such CA IX targeted therapies.

ATCC Deposits

The materials listed below were deposited with the American Type Culture Collection (ATCC) now at 10810 University Blvd., Manassus, Va. 20110-2209 (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas and plasmids will be made available by the ATCC under the terms of the Budapest Treaty, and subject to an agreement between the Applicants and the ATCC which assures unrestricted availability of the deposited hybridomas and plasmids to the public upon the granting of patent from the instant application. Availability of the deposits is not to be construed as a license to practice the invention in contravention of the rights granted under the authority of any Government in accordance with its patent laws.

|  | Deposit Date | ATCC # |
|---|---|---|
| Hybridoma |  |  |
| VU-M75 | Sep. 17, 1992 | HB 11128 |
| MN 12.2.2 | Jun. 9, 1994 | HB 11647 |
| Plasmid |  |  |
| A4a | Jun. 6, 1995 | 97199 |
| XE1 | Jun. 6, 1995 | 97200 |
| XE3 | Jun. 6, 1995 | 97198 |

Similarly, the hybridoma cell line V/10-VU which produces the V/10 monoclonal antibodies was deposited on Feb. 19, 2003 under the Budapest Treaty at the International Depository Authority (IDA) of the Belgian Coordinated Collections of Microorganisms (BCCM) at the Laboratorium voor Moleculaire Biologie-Plasmidencollectie (LMBP) at the Universeit Gent, K. L. Ledeganckstraat 35, B-9000 Gent, Belgium [BCCM/LMBP] under the Accession No. LMBP 6009CB.

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

The invention claimed is:

1. A method of inhibiting EGF receptor dependent signaling on the phosphorylation of carbonic anhydrase 9 (MN/CA IX) in a human subject with renal cell carcinoma, wherein said disease is characterized by abnormal MN/CA9 gene expression, comprising:
   (a) obtaining a sample of body fluid or preneoplastic/neoplastic tissue from said human;
   (b) detecting and quantifying the level of MN/CA9 gene expression product in said sample; and
   (c) if said MN/CA9 gene expression product level in said sample is increased as compared to normal control, administering to said human a therapeutically effective amount of a composition comprising an EGFR tyrosine kinase inhibitor
   wherein said tyrosine kinase inhibitor inhibits EGFR dependent phosphorylation of MN/CA IX.

2. The method of claim 1, wherein said tyrosine kinase inhibitor is selected from the group consisting of gefitinib, erlotinib, lapatinib, canertinib, and EKB-569.

3. The method of claim 1, wherein said EGFR tyrosine kinase inhibitor is conjugated to an antibody or a binding fragment thereof which specifically binds MN/CA IX.

4. The method of claim 1 further comprising administering to said human radiation and/or a therapeutically effective amount in a physiologically acceptable formulation of one or more of the following compounds selected from the group consisting of: conventional anticancer drug, chemotherapeutic agent, Sorafenib (BAY 43-9006), an omega-carboxypyridyl substituted urea, MN/CA IX-specific antibody or a binding fragment thereof.

* * * * *

SEQUENCE LISTING

```
<160> NUMBER OF SEQ ID NOS: 31

<210> SEQ ID NO 1
<211> LENGTH: 1522
<212> TYPE: DNA
<213> ORGANISM: Homo sapiens
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 1
acagtcagcc gc atg gct ccc ctg tgc ccc agc ccc tgg ctc cct ctg ttg        51
          Met Ala Pro Leu Cys Pro Ser Pro Trp Leu Pro Leu Leu
                  -35              -30              -25 atc ccg gcc cct gct cca ggc ctc act gtg caa ctg ctg ctg tca ctg           99
Ile Pro Ala Pro Ala Pro Gly Leu Thr Val Gln Leu Leu Leu Ser Leu
              -20              -15              -10 ctg ctt ctg atg cct gtc cat ccc cag agg ttg ccc cgg atg cag gag          147
Leu Leu Leu Met Pro Val His Pro Gln Arg Leu Pro Arg Met Gln Glu
          -5               -1  1                   5 gat tcc ccc ttg gga gga ggc tct tct ggg gaa gat gac cca ctg ggc          195
Asp Ser Pro Leu Gly Gly Gly Ser Ser Gly Glu Asp Asp Pro Leu Gly
     10                  15                  20 gag gag gat ctg ccc agt gaa gag gat tca ccc aga gag gag gat cca          243
Glu Glu Asp Leu Pro Ser Glu Glu Asp Ser Pro Arg Glu Glu Asp Pro
25                  30                  35                  40 ccc gga gag gag gat cta cct gga gag gag gat cta cct gga gag gag          291
Pro Gly Glu Glu Asp Leu Pro Gly Glu Glu Asp Leu Pro Gly Glu Glu
                 45                  50                  55 gat cta cct gaa gtt aag cct aaa tca gaa gaa gag ggc tcc ctg aag          339
Asp Leu Pro Glu Val Lys Pro Lys Ser Glu Glu Glu Gly Ser Leu Lys
              60                  65                  70 tta gag gat cta cct act gtt gag gct cct gga gat cct caa gaa ccc          387
Leu Glu Asp Leu Pro Thr Val Glu Ala Pro Gly Asp Pro Gln Glu Pro
          75                  80                  85
```

-continued

| | |
|---|---|
| cag aat aat gcc cac agg gac aaa gaa ggg gat gac cag agt cat tgg<br>Gln Asn Asn Ala His Arg Asp Lys Glu Gly Asp Asp Gln Ser His Trp<br>90                       95                    100 | 435 |
| cgc tat gga ggc gac ccg ccc tgg ccc cgg gtg tcc cca gcc tgc gcg<br>Arg Tyr Gly Gly Asp Pro Pro Trp Pro Arg Val Ser Pro Ala Cys Ala<br>105                    110                  115                  120 | 483 |
| ggc cgc ttc cag tcc ccg gtg gat atc cgc ccc cag ctc gcc gcc ttc<br>Gly Arg Phe Gln Ser Pro Val Asp Ile Arg Pro Gln Leu Ala Ala Phe<br>                    125                  130                  135 | 531 |
| tgc ccg gcc ctg cgc ccc ctg gaa ctc ctg ggc ttc cag ctc ccg ccg<br>Cys Pro Ala Leu Arg Pro Leu Glu Leu Leu Gly Phe Gln Leu Pro Pro<br>            140                  145                  150 | 579 |
| ctc cca gaa ctg cgc ctg cgc aac aat ggc cac agt gtg caa ctg acc<br>Leu Pro Glu Leu Arg Leu Arg Asn Asn Gly His Ser Val Gln Leu Thr<br>          155                  160                  165 | 627 |
| ctg cct cct ggg cta gag atg gct ctg ggt ccc ggg cgg gag tac cgg<br>Leu Pro Pro Gly Leu Glu Met Ala Leu Gly Pro Gly Arg Glu Tyr Arg<br>170                       175                  180 | 675 |
| gct ctg cag ctg cat ctg cac tgg ggg gct gca ggt cgt ccg ggc tcg<br>Ala Leu Gln Leu His Leu His Trp Gly Ala Ala Gly Arg Pro Gly Ser<br>185                       190                  195                  200 | 723 |
| gag cac act gtg gaa ggc cac cgt ttc cct gcc gag atc cac gtg gtt<br>Glu His Thr Val Glu Gly His Arg Phe Pro Ala Glu Ile His Val Val<br>                    205                  210                  215 | 771 |
| cac ctc agc acc gcc ttt gcc aga gtt gac gag gcc ttg ggg cgc ccg<br>His Leu Ser Thr Ala Phe Ala Arg Val Asp Glu Ala Leu Gly Arg Pro<br>            220                  225                  230 | 819 |
| gga ggc ctg gcc gtg ttg gcc gcc ttt ctg gag gag ggc ccg gaa gaa<br>Gly Gly Leu Ala Val Leu Ala Ala Phe Leu Glu Glu Gly Pro Glu Glu<br>          235                  240                  245 | 867 |
| aac agt gcc tat gag cag ttg ctg tct cgc ttg gaa gaa atc gct gag<br>Asn Ser Ala Tyr Glu Gln Leu Leu Ser Arg Leu Glu Glu Ile Ala Glu<br>250                       255                  260 | 915 |
| gaa ggc tca gag act cag gtc cca gga ctg gac ata tct gca ctc ctg<br>Glu Gly Ser Glu Thr Gln Val Pro Gly Leu Asp Ile Ser Ala Leu Leu<br>265                       270                  275                  280 | 963 |
| ccc tct gac ttc agc cgc tac ttc caa tat gag ggg tct ctg act aca<br>Pro Ser Asp Phe Ser Arg Tyr Phe Gln Tyr Glu Gly Ser Leu Thr Thr<br>                    285                  290                  295 | 1011 |
| ccg ccc tgt gcc cag ggt gtc atc tgg act gtg ttt aac cag aca gtg<br>Pro Pro Cys Ala Gln Gly Val Ile Trp Thr Val Phe Asn Gln Thr Val<br>            300                  305                  310 | 1059 |
| atg ctg agt gct aag cag ctc cac acc ctc tct gac acc ctg tgg gga<br>Met Leu Ser Ala Lys Gln Leu His Thr Leu Ser Asp Thr Leu Trp Gly<br>          315                  320                  325 | 1107 |
| cct ggt gac tct cgg cta cag ctg aac ttc cga gcg acg cag cct ttg<br>Pro Gly Asp Ser Arg Leu Gln Leu Asn Phe Arg Ala Thr Gln Pro Leu<br>330                       335                  340 | 1155 |
| aat ggg cga gtg att gag gcc tcc ttc cct gct gga gtg gac agc agt<br>Asn Gly Arg Val Ile Glu Ala Ser Phe Pro Ala Gly Val Asp Ser Ser<br>345                       350                  355                  360 | 1203 |
| cct cgg gct gct gag cca gtc cag ctg aat tcc tgc ctg gct gct ggt<br>Pro Arg Ala Ala Glu Pro Val Gln Leu Asn Ser Cys Leu Ala Ala Gly<br>                    365                  370                  375 | 1251 |
| gac atc cta gcc ctg gtt ttt ggc ctc ctt ttt gct gtc acc agc gtc<br>Asp Ile Leu Ala Leu Val Phe Gly Leu Leu Phe Ala Val Thr Ser Val<br>            380                  385                  390 | 1299 |
| gcg ttc ctt gtg cag atg aga agg cag cac aga agg gga acc aaa ggg<br>Ala Phe Leu Val Gln Met Arg Arg Gln His Arg Arg Gly Thr Lys Gly<br>395                       400                  405 | 1347 |

-continued

```
ggt gtg agc tac cgc cca gca gag gta gcc gag act gga gcc              1389
Gly Val Ser Tyr Arg Pro Ala Glu Val Ala Glu Thr Gly Ala
    410                 415                 420 tagaggctgg atcttggaga atgtgagaag ccagccagag gcatctgagg gggagccggt    1449
aactgtcctg tcctgctcat tatgccactt cctttaact gccagaaat ttttaaaat      1509 aaatatttat aat                                                       1522
```

<210> SEQ ID NO 2
<211> LENGTH: 459
<212> TYPE: PRT
<213> ORGANISM: Homo sapiens

<400> SEQUENCE: 2

```
Met Ala Pro Leu Cys Pro Ser Pro Trp Leu Pro Leu Leu Ile Pro Ala
        -35                 -30                 -25

Pro Ala Pro Gly Leu Thr Val Gln Leu Leu Leu Ser Leu Leu Leu Leu
    -20                 -15                 -10

Met Pro Val His Pro Gln Arg Leu Pro Arg Met Gln Glu Asp Ser Pro
-5          -1   1               5                      10

Leu Gly Gly Gly Ser Ser Gly Glu Asp Asp Pro Leu Gly Glu Glu Asp
                15                  20                  25

Leu Pro Ser Glu Glu Asp Ser Pro Arg Glu Glu Asp Pro Pro Gly Glu
            30                  35                  40

Glu Asp Leu Pro Gly Glu Glu Asp Leu Pro Gly Glu Glu Asp Leu Pro
        45                  50                  55

Glu Val Lys Pro Lys Ser Glu Glu Gly Ser Leu Lys Leu Glu Asp
60                  65                  70                  75

Leu Pro Thr Val Glu Ala Pro Gly Asp Pro Gln Glu Pro Gln Asn Asn
                80                  85                  90

Ala His Arg Asp Lys Glu Gly Asp Asp Gln Ser His Trp Arg Tyr Gly
            95                  100                 105

Gly Asp Pro Pro Trp Pro Arg Val Ser Pro Ala Cys Ala Gly Arg Phe
        110                 115                 120

Gln Ser Pro Val Asp Ile Arg Pro Gln Leu Ala Ala Phe Cys Pro Ala
    125                 130                 135

Leu Arg Pro Leu Glu Leu Leu Gly Phe Gln Leu Pro Pro Leu Pro Glu
140                 145                 150                 155

Leu Arg Leu Arg Asn Asn Gly His Ser Val Gln Leu Thr Leu Pro Pro
                160                 165                 170

Gly Leu Glu Met Ala Leu Gly Pro Gly Arg Glu Tyr Arg Ala Leu Gln
            175                 180                 185

Leu His Leu His Trp Gly Ala Ala Gly Arg Pro Gly Ser Glu His Thr
        190                 195                 200

Val Glu Gly His Arg Phe Pro Ala Glu Ile His Val Val His Leu Ser
    205                 210                 215

Thr Ala Phe Ala Arg Val Asp Glu Ala Leu Gly Arg Pro Gly Gly Leu
220                 225                 230                 235

Ala Val Leu Ala Ala Phe Leu Glu Glu Gly Pro Glu Glu Asn Ser Ala
                240                 245                 250

Tyr Glu Gln Leu Leu Ser Arg Leu Glu Ile Ala Glu Glu Gly Ser
            255                 260                 265

Glu Thr Gln Val Pro Gly Leu Asp Ile Ser Ala Leu Leu Pro Ser Asp
        270                 275                 280
```

```
Phe Ser Arg Tyr Phe Gln Tyr Glu Gly Ser Leu Thr Thr Pro Pro Cys
    285                 290                 295
Ala Gln Gly Val Ile Trp Thr Val Phe Asn Gln Thr Val Met Leu Ser
300                 305                 310                 315
Ala Lys Gln Leu His Thr Leu Ser Asp Thr Leu Trp Gly Pro Gly Asp
                320                 325                 330
Ser Arg Leu Gln Leu Asn Phe Arg Ala Thr Gln Pro Leu Asn Gly Arg
            335                 340                 345
Val Ile Glu Ala Ser Phe Pro Ala Gly Val Asp Ser Ser Pro Arg Ala
        350                 355                 360
Ala Glu Pro Val Gln Leu Asn Ser Cys Leu Ala Ala Gly Asp Ile Leu
    365                 370                 375
Ala Leu Val Phe Gly Leu Leu Phe Ala Val Thr Ser Val Ala Phe Leu
380                 385                 390                 395
Val Gln Met Arg Arg Gln His Arg Arg Gly Thr Lys Gly Gly Val Ser
                400                 405                 410
Tyr Arg Pro Ala Glu Val Ala Glu Thr Gly Ala
            415                 420

<210> SEQ ID NO 3
<211> LENGTH: 10898
<212> TYPE: DNA
<213> ORGANISM: Homo sapiens
<220> FEATURE:
<221> NAME/KEY: gene
<222> LOCATION: (1)..(10898)
<220> FEATURE:
<221> NAME/KEY: misc_feature
<222> LOCATION: (1974)..(1974)
<223> OTHER INFORMATION: n is a, c, g, or t

<400> SEQUENCE: 3
ggatcctgtt gactcgtgac cttaccccca accctgtgct ctctgaaaca tgagctgtgt     60
ccactcaggg ttaaatggat taagggcggt gcaagatgtg ctttgttaaa cagatgcttg    120
aaggcagcat gctcgttaag agtcatcacc aatccctaat ctcaagtaat cagggacaca    180
aacactgcgg aaggccgcag ggtcctctgc ctaggaaaac cagagacctt tgttcacttg    240
tttatctgac cttccctcca ctattgtcca tgaccctgcc aaatccccct ctgtgagaaa    300
cacccaagaa ttatcaataa aaaataaatt taaaaaaaa aatacaaaaa aaaaaaaaa    360
aaaaaaaaaa gacttacgaa tagttattga taaatgaata gctattggta aagccaagta    420
aatgatcata ttcaaaacca gacggccatc atcacagctc aagtctacct gatttgatct    480
ctttatcatt gtcattcttt ggattcacta gattagtcat catcctcaaa attctccccc    540
aagttctaat tacgttccaa acatttaggg gttacatgaa gcttgaacct actaccttct    600
ttgcttttga gccatgagtt gtaggaatga tgagtttaca ccttacatgc tggggattaa    660
tttaaacttt acctctaagt cagttgggta gcctttggct tattttgta gctaattttg    720
tagttaatgg atgcactgtg aatcttgcta tgatagtttt cctccacact ttgccactag    780
gggtaggtag gtactcagtt ttcagtaatt gcttacctaa gaccctaagc cctatttctc    840
ttgtactggc ctttatctgt aatatgggca tatttaatac aatataattt tggagttttt    900
tttgtttgtt tgtttgtttg ttttttgag acgagtcttt gcatctgtca tgcccaggct    960
ggagtagcag tggtgccatc tcggctcact gcaagctcca cctcccgagt tcacgccatt   1020
ttcctgcctc agcctcccga gtagctggga ctacaggcgc cgccaccat gcccggctaa    1080
tttttttgtat ttttggtaga gacggggttt caccgtgtta gccagaatgg tctcgatctc   1140
```

```
ctgacttcgt gatccacccg cctcggcctc ccaaagttct gggattacag gtgtgagcca    1200
ccgcacctgg ccaattttt gagtctttta aagtaaaaat atgtcttgta agctggtaac     1260
tatggtacat ttccttttat taatgtggtg ctgacggtca tataggttct tttgagtttg    1320
gcatgcatat gctacttttt gcagtccttt cattacatt ttctctcttc atttgaagag    1380
catgttatat cttttagctt cacttggctt aaaaggttct ctcattagcc taacacagtg    1440
tcattgttgg taccacttgg atcataagtg gaaaacagt caagaaattg cacagtaata    1500
cttgtttgta agagggatga ttcaggtgaa tctgacacta agaaactccc ctacctgagg    1560
tctgagattc ctctgacatt gctgtatata ggcttttcct ttgacagcct gtgactgcgg    1620
actatttttc ttaagcaaga tatgctaaag ttttgtgagc ctttttccag agagaggtct    1680
catatctgca tcaagtgaga acatataatg tctgcatgtt tccatatttc aggaatgttt    1740
gcttgtgttt tatgctttta tatagacagg gaaacttgtt cctcagtgac caaaagagg    1800
tgggaattgt tattggatat catcattggc ccacgctttc tgaccttgga aacaattaag    1860
ggttcataat ctcaattctg tcagaattgg tacaagaaat agctgctatg tttcttgaca    1920
ttccacttgg taggaaataa gaatgtgaaa ctcttcagtt ggtgtgtgtc cctngttttt    1980
ttgcaatttc cttcttactg tgttaaaaaa aagtatgatc ttgctctgag aggtgaggca    2040
ttcttaatca tgatctttaa agatcaataa tataatcctt tcaaggatta tgtctttatt    2100
ataataaaga taatttgtct ttaacagaat caataatata atcccttaaa ggattatatc    2160
tttgctgggc gcagtggctc acacctgtaa tcccagcact ttgggtggcc aaggtggaag    2220
gatcaaattt gcctacttct atattatctt ctaaagcaga attcatctct cttccctcaa    2280
tatgatgata ttgacagggt tgccctcac tcactagatt gtgagctcct gctcagggca    2340
ggtagcgttt tttgttttg ttttttgttt tcttttttga cagggtct tgctctgtca    2400
cccaggccag agtgcaatgg tacagtctca gctcactgca gcctcaaccg cctcggctca    2460
aaccatcatc ccatttcagc ctcctgagta gctgggacta caggcacatg ccattacacc    2520
tggctaattt ttttgtattt ctagtagaga caggggtttgg ccatgttgcc cgggctggtc    2580
tcgaactcct ggactcaagc aatccaccca cctcagcctc ccaaaatgag ggaccgtgtc    2640
ttattcattt ccatgtccct agtccatagc ccagtgctgg acctatggta gtactaaata    2700
aatatttgtt gaatgcaata gtaaatagca tttcagggag caagaactag attaacaaag    2760
gtggtaaaag gtttggagaa aaaataata gtttaatttg gctagagtat gagggagagt    2820
agtaggagac aagatggaaa ggtctcttgg gcaaggtttt gaaggaagtt ggaagtcaga    2880
agtacacaat gtgcatatcg tggcaggcag tggggagcca atgaaggctt ttgagcagga    2940
gagtaatgtg ttgaaaaata aatataggtt aaacctatca gagcccctct gacacataca    3000
cttgcttttc attcaagctc aagtttgtct cccacatacc cattacttaa ctcaccctcg    3060
ggctccccta gcagcctgcc ctacctcttt acctgcttcc tggtggagtc agggatgtat    3120
acatgagctg cttcccctct cagccagagg acatggggg ccccagctcc cctgcctttc    3180
cccttctgtg cctggagctg ggaagcaggc cagggttagc tgaggctggc tggcaagcag    3240
ctgggtggtg ccagggagag cctgcatagt gccaggtggt gccttgggtt ccaagctagt    3300
ccatggcccc gataaccttc tgcctgtgca cacacctgcc cctcactcca ccccatcct    3360
agctttggta tgggggagag ggcacagggc cagacaaacc tgtgagactt tggctccatc    3420
tctgcaaaag ggcgctctgt gagtcagcct gctccctcc aggcttgctc ctcccccacc    3480
```

```
cagctctcgt ttccaatgca cgtacagccc gtacacaccg tgtgctggga cacccacag    3540 tcagccgcat ggctcccctg tgcccagcc cctggctccc tctgttgatc ccggcccctg    3600
ctccaggcct cactgtgcaa ctgctgctgt cactgctgct tctggtgcct gtccatcccc    3660
agaggttgcc ccggatgcag gaggattccc ccttgggagg aggctcttct ggggaagatg    3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag gacaaagaa ggtaagtggt    3960 catcaatctc caaatccagg ttccaggagg ttcatgactc ccctcccata ccccagccta    4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200 tggagaagag aaagggatga gaactgcaga tgagagaaaa aatgtgcaga cagaggaaaa    4260
aaataggtgg agaaggagag tcagagagtt tgaggggaag agaaaaggaa agcttgggag    4320
gtgaagtggg taccagagac aagcaagaag agctggtaga agtcatctca tcttaggcta    4380
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt ttttttttt ttttgagac aaactttcac ttttgttgcc    4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
ccggctaatt tttgtatttt tagtagagac ggggtttcgc catgttggtc aggctggtct    4800
cgaactcctg atctcaggtg atccaaccac cctggcctcc caaagtgctg ggattatagg    4860
cgtgagccac agcgcctggc ctgaagcagc cactcacttt tacagaccct aagcaaatga    4920
ttgcaagctg gtaggattgc tgtttggccc acccagctgc ggtgttgagt ttgggtgcgg    4980
tctcctgtgc tttgcacctg gcccgcttaa ggcatttgtt acccgtaatg ctcctgtaag    5040
gcatctgcgt ttgtgacatc gttttggtcg ccaggaaggg attggggctc taagcttgag    5100
cggttcatcc ttttcattta tacaggggat gaccagagtc attggcgcta tggaggtgag    5160
acacccaccc gctgcacaga cccaatctgg gaacccagct ctgtggatct cccctacagc    5220
cgtccctgaa cactggtccc gggcgtccca cccgccgccc accgtccac cccctcacct    5280 tttctacccg ggttccctaa gttcctgacc taggcgtcag acttcctcac tatactctcc    5340 cacccaggc gacccgccct ggccccgggt gtccccagcc tgcgcgggcc gcttccagtc    5400
cccggtggat atccgccccc agctcgccgc cttctgcccg gccctgcgcc cctggaact    5460 cctgggcttc cagctcccgc cgctcccaga actgcgcctg cgcaacaatg ccacagtgg    5520 tgaggggtc tccccgccga cttgggga tggggcgggg cgcagggaag gaaccgtcg    5580 cgcagtgcct gcccgggggt tgggctggcc ctaccgggcg gggccggctc acttgcctct    5640
ccctacgcag tgcaactgac cctgcctcct gggctagaga tggctctggg tcccgggcgg    5700
gagtaccggg ctctgcagct gcatctgcac tggggggctg caggtcgtcc gggctcggag    5760
cacactgtga aaggccaccg tttccctgcc gaggtgagcg cggactggcc gagaaggggc    5820
aaaggagcgg ggcggacggg ggccagagac gtggccctct cctaccctcg tgtccttttc    5880
```

```
agatccacgt ggttcacctc agcaccgcct tgccagagt tgacgaggcc ttggggcgcc    5940
cgggaggcct ggccgtgttg ccgcctttc tggaggtacc agatcctgga cacccctac    6000 tccccgcttt cccatcccat gctcctcccg gactctatcg tggagccaga gaccccatcc    6060
cagcaagctc actcaggccc ctggctgaca aactcattca cgcactgttt gttcatttaa    6120
cacccactgt gaaccaggca ccagccccca acaaggattc tgaagctgta ggtccttgcc    6180
tctaaggagc ccacagccag tgggggaggc tgacatgaca gacacatagg aaggacatag    6240
taaagatggt ggtcacagag gaggtgacac ttaaagcctt cactggtaga aaagaaaagg    6300
aggtgttcat tgcagaggaa acagaatgtg caaagactca gaatatggcc tatttaggga    6360
atggctacat acaccatgat tagaggaggc ccagtaaagg gaagggatgg tgagatgcct    6420
gctaggttca ctcactcact tttatttatt tatttatttt tttgacagtc tctctgtcgc    6480
ccaggctgga gtgcagtggt gtgatcttgg gtcactgcaa cttccgcctc ccgggttcaa    6540
gggattctcc tgcctcagct tcctgagtag ctggggttac aggtgtgtgc caccatgccc    6600
agctaatttt tttttgtatt tttagtagac agggtttcac catgttggtc aggctggtct    6660
caaactcctg gcctcaagtg atccgcctga ctcagcctac caaagtgctg attacaagtg    6720
tgagccaccg tgcccagcca cactcactga ttctttaatg ccagccacac agcacaaagt    6780
tcagagaaat gcctccatca tagcatgtca atatgttcat actcttaggt tcatgatgtt    6840
cttaacatta ggttcataag caaaataaga aaaagaata ataaataaaa gaagtggcat    6900
gtcaggacct cacctgaaaa gccaaacaca gaatcatgaa ggtgaatgca gaggtgacac    6960
caacacaaag gtgtatatat ggtttcctgt ggggagtatg tacggaggca gcagtgagtg    7020
agactgcaaa cgtcagaagg gcacgggtca ctgagagcct agtatcctag taaagtgggc    7080
tctctccctc tctctccagc ttgtcattga aaaccagtcc accaagcttg ttggttcgca    7140
cagcaagagt acatagagtt tgaaataata cataggattt taagagggag acactgtctc    7200
taaaaaaaaa aacaacagca acaacaaaaa gcaacaacca ttacaatttt atgttccctc    7260
agcattctca gagctgagga atgggagagg actatgggaa cccccttcat gttccggcct    7320
tcagccatgg ccctggatac atgcactcat ctgtcttaca atgtcattcc cccaggaggg    7380 cccgaagaa aacagtgcct atgagcagtt gctgtctcgc ttggaagaaa tcgctgagga    7440
aggtcagttt gttggtctgg ccactaatct ctgtggccta gttcataaag aatcacccett    7500 tggagcttca ggtctgaggc tggagatggg ctccctccag tgcaggaggg attgaagcat    7560
gagccagcgc tcatcttgat aataaccatg aagctgacag acacagttac ccgcaaacgg    7620
ctgcctacag attgaaaacc aagcaaaaac cgccgggcac ggtggctcac gcctgtaatc    7680
ccagcacttt gggaggccaa ggcaggtgga tcacgaggtc aagagatcaa gaccatcctg    7740
gccaacatgt gaaacccca tctctactaa aaatacgaaa aaatagccag gcgtggtggc    7800
gggtgcctgt aatcccagct actcgggagg ctgaggcagg agaatggcat gaacccggga    7860
ggcagaagtt gcagtgagcc gagatcgtgc cactgcactc cagcctgggc aacagagcga    7920
gactcttgtc tcaaaaaaaa aaaaaaaaaa gaaaaccaag caaaaaccaa aatgagacaa    7980
aaaaaacaag accaaaaaat ggtgtttgga aattgtcaag gtcaagtctg gagagctaaa    8040 cttttctga gaactgttta tctttaataa gcatcaaata ttttaacttt gtaaatactt    8100
ttgttggaaa tcgttctctt cttagtcact cttgggtcat tttaaatctc acttactcta    8160 ctagacctt taggtttctg ctagactagg tagaactctg cctttgcatt tcttgtgtct    8220
```

-continued

```
gttttgtata gttatcaata ttcatattta tttacaagtt attcagatca tttttttctttt  8280
tcttttttttt tttttttttt tttttttacat ctttagtaga gacagggttt caccatattg  8340
gccaggctgc tctcaaactc ctgaccttgt gatccaccag cctcggcctc ccaaagtgct    8400
gggattcatt ttttcttttt aatttgctct gggcttaaac ttgtggccca gcactttatg   8460
atggtacaca gagttaagag tgtagactca gacggtcttt cttctttcct tctcttcctt    8520
cctcccttcc ctcccacctt cccttctctc cttcctttct ttcttcctct cttgcttcct    8580
caggcctctt ccagttgctc caaagccctg tactttttt tgagttaacg tcttatggga    8640
agggcctgca cttagtgaag aagtggtctc agagttgagt taccttggct tctgggaggt    8700
gaaactgtat ccctatacccc tgaagcttta aggggtgca atgtagatga accccaaca    8760
tagatcctct tcacaggctc agagactcag gtcccaggac tggacatatc tgcactcctg   8820
ccctctgact tcagccgcta cttccaatat gaggggtctc tgactacacc gccctgtgcc   8880
cagggtgtca tctggactgt gtttaaccag acagtgatgc tgagtgctaa gcaggtgggc   8940
ctggggtgtg tgtggacaca gtgggtgcgg gggaagagg atgtaagatg agatgagaaa    9000
caggagaaga aagaaatcaa ggctgggctc tgtggcttac gcctataatc ccaccacgtt    9060
gggaggctga ggtgggagaa tggtttgagc ccaggagttc aagacaaggc ggggcaacat   9120
agtgtgaccc catctctacc aaaaaaaccc caacaaaacc aaaaatagcc gggcatggtg   9180
gtatgcggcc tagtcccagc tactcaagga ggctgaggtg ggaagatcgc ttgattccag   9240
gagtttgaga ctgcagtgag ctatgatccc accactgcct accatcttta ggatacattt    9300
atttatttat aaaagaaatc aagaggctgg atggggaata caggagctgg agggtggagc    9360
cctgaggtgc tggttgtgag ctggcctggg acccttgttt cctgtcatgc catgaaccca    9420
cccacactgt ccactgacct ccctagctcc acaccctctc tgacaccctg tggggacctg   9480
gtgactctcg gctacagctg aacttccgag cgacgcagcc tttgaatggg cgagtgattg    9540
aggcctcctt ccctgctgga gtggacagca gtcctcgggc tgctgagcca ggtacagctt    9600
tgtctggttt cccccagcc agtagtccct tatcctccca tgtgtgtgcc agtgtctgtc    9660
attggtggtc acagcccgcc tctcacatct ccttttctc tccagtccag ctgaattcct    9720
gcctggctgc tggtgagtct gcccctcctc ttggtcctga tgccaggaga ctcctcagca    9780
ccattcagcc ccagggctgc tcaggaccgc ctctgctccc tctcctttttc tgcagaacag   9840
accccaaccc caatattaga gaggcagatc atggtgggga ttcccccatt gtccccagag    9900
gctaattgat tagaatgaag cttgagaaat ctcccagcat ccctctcgca aaagaatccc    9960
cccccctttt tttaaagata gggtctcact ctgtttgccc caggctgggg tgttgtggca   10020
cgatcatagc tcactgcagc ctcgaactcc taggctcagg caatcctttc accttagctt   10080
ctcaaagcac tgggactgta ggcatgagcc actgtgcctg gccccaaacg gccctttac    10140
ttggcttttta ggaagcaaaa acggtgctta tcttacccct tctcgtgtat ccaccctcat   10200
cccttggctg gcctcttctg gagactgagg cactatgggg ctgcctgaga actcggggca   10260
ggggtggtgg agtgcactga ggcaggtgtt gaggaactct gcagacccct cttccttccc   10320
aaagcagccc tctctgctct ccatcgcagg tgacatccta gccctggttt ttggcctcct   10380
ttttgctgtc accagcgtcg cgttccttgt gcagatgaga aggcagcaca ggtattacac   10440
tgaccctttc ttcaggcaca agcttccccc acccttgtgg agtcacttca tgcaaagcgc   10500
atgcaaatga gctgctcctg ggccagtttt ctgattagcc tttcctgttg tgtacacaca   10560
gaaggggaac caaaggggt gtgagctacc gcccagcaga ggtagccgag actggagcct   10620
```

```
agaggctgga tcttggagaa tgtgagaagc cagccagagg catctgaggg ggagccggta   10680
actgtcctgt cctgctcatt atgccacttc cttttaactg ccaagaaatt ttttaaaata   10740
aatatttata ataaaatatg tgttagtcac ctttgttccc caaatcagaa ggaggtattt   10800
gaatttccta ttactgttat tagcaccaat ttagtggtaa tgcatttatt ctattacagt   10860
tcggcctcct tccacacatc actccaatgt gttgctcc                           10898
```

<210> SEQ ID NO 4
<211> LENGTH: 37
<212> TYPE: PRT
<213> ORGANISM: Homo sapiens

<400> SEQUENCE: 4

```
Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Met Pro Val His Pro
        35
```

<210> SEQ ID NO 5
<211> LENGTH: 377
<212> TYPE: PRT
<213> ORGANISM: Homo sapiens

<400> SEQUENCE: 5

```
Gln Arg Leu Pro Arg Met Gln Glu Asp Ser Pro Leu Gly Gly Gly Ser
1               5                   10                  15

Ser Gly Glu Asp Asp Pro Leu Gly Glu Glu Asp Leu Pro Ser Glu Glu
            20                  25                  30

Asp Ser Pro Arg Glu Glu Asp Pro Gly Glu Glu Asp Leu Pro Gly
            35                  40                  45

Glu Glu Asp Leu Pro Gly Glu Glu Asp Leu Pro Glu Val Lys Pro Lys
50                  55                  60

Ser Glu Glu Glu Gly Ser Leu Lys Leu Glu Asp Leu Pro Thr Val Glu
65                  70                  75                  80

Ala Pro Gly Asp Pro Gln Glu Pro Gln Asn Asn Ala His Arg Asp Lys
                85                  90                  95

Glu Gly Asp Asp Gln Ser His Trp Arg Tyr Gly Gly Asp Pro Pro Trp
            100                 105                 110

Pro Arg Val Ser Pro Ala Cys Ala Gly Arg Phe Gln Ser Pro Val Asp
        115                 120                 125

Ile Arg Pro Gln Leu Ala Ala Phe Cys Pro Ala Leu Arg Pro Leu Glu
    130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Pro Gly Leu Glu Met Ala
                165                 170                 175

Leu Gly Pro Gly Arg Glu Tyr Arg Ala Leu Gln Leu His Leu His Trp
            180                 185                 190

Gly Ala Ala Gly Arg Pro Gly Ser Glu His Thr Val Glu Gly His Arg
        195                 200                 205

Phe Pro Ala Glu Ile His Val Val His Leu Ser Thr Ala Phe Ala Arg
    210                 215                 220

Val Asp Glu Ala Leu Gly Arg Pro Gly Gly Leu Ala Val Leu Ala Ala
```

-continued

```
                    225                 230                 235                 240
Phe Leu Glu Glu Gly Pro Glu Glu Asn Ser Ala Tyr Glu Gln Leu Leu
                245                 250                 255

Ser Arg Leu Glu Glu Ile Ala Glu Gly Ser Glu Thr Gln Val Pro
            260                 265                 270

Gly Leu Asp Ile Ser Ala Leu Leu Pro Ser Asp Phe Ser Arg Tyr Phe
            275                 280                 285

Gln Tyr Glu Gly Ser Leu Thr Thr Pro Pro Cys Ala Gln Gly Val Ile
        290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
            340                 345                 350

Phe Pro Ala Gly Val Asp Ser Ser Pro Arg Ala Ala Glu Pro Val Gln
        355                 360                 365

Leu Asn Ser Cys Leu Ala Ala Gly Asp
    370                 375

<210> SEQ ID NO 6
<211> LENGTH: 20
<212> TYPE: PRT
<213> ORGANISM: Homo sapiens

<400> SEQUENCE: 6

Ile Leu Ala Leu Val Phe Gly Leu Leu Phe Ala Val Thr Ser Val Ala
1               5                   10                  15

Phe Leu Val Gln
            20

<210> SEQ ID NO 7
<211> LENGTH: 25
<212> TYPE: PRT
<213> ORGANISM: Homo sapiens

<400> SEQUENCE: 7

Met Arg Arg Gln His Arg Arg Gly Thr Lys Gly Gly Val Ser Tyr Arg
1               5                   10                  15

Pro Ala Glu Val Ala Glu Thr Gly Ala
            20                  25

<210> SEQ ID NO 8
<211> LENGTH: 59
<212> TYPE: PRT
<213> ORGANISM: Homo sapiens

<400> SEQUENCE: 8

Ser Ser Gly Glu Asp Asp Pro Leu Gly Glu Glu Asp Leu Pro Ser Glu
1               5                   10                  15

Glu Asp Ser Pro Arg Glu Glu Asp Pro Pro Gly Glu Glu Asp Leu Pro
            20                  25                  30

Gly Glu Glu Asp Leu Pro Gly Glu Glu Asp Leu Pro Glu Val Lys Pro
        35                  40                  45

Lys Ser Glu Glu Glu Gly Ser Leu Lys Leu Glu
    50                  55

<210> SEQ ID NO 9
```

<211> LENGTH: 257
<212> TYPE: PRT
<213> ORGANISM: Homo sapiens

<400> SEQUENCE: 9

```
Gly Asp Asp Gln Ser His Trp Arg Tyr Gly Asp Pro Pro Trp Pro
1               5                   10                  15

Arg Val Ser Pro Ala Cys Ala Gly Arg Phe Gln Ser Pro Val Asp Ile
            20                  25                  30

Arg Pro Gln Leu Ala Ala Phe Cys Pro Ala Leu Arg Pro Leu Glu Leu
        35                  40                  45

Leu Gly Phe Gln Leu Pro Pro Leu Pro Glu Leu Arg Leu Arg Asn Asn
    50                  55                  60

Gly His Ser Val Gln Leu Thr Leu Pro Pro Gly Leu Glu Met Ala Leu
65                  70                  75                  80

Gly Pro Gly Arg Glu Tyr Arg Ala Leu Gln Leu His Leu His Trp Gly
                85                  90                  95

Ala Ala Gly Arg Pro Gly Ser Glu His Thr Val Glu Gly His Arg Phe
            100                 105                 110

Pro Ala Glu Ile His Val Val His Leu Ser Thr Ala Phe Ala Arg Val
        115                 120                 125

Asp Glu Ala Leu Gly Arg Pro Gly Gly Leu Ala Val Leu Ala Ala Phe
    130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Glu Gly Ser Glu Thr Gln Val Pro Gly
                165                 170                 175

Leu Asp Ile Ser Ala Leu Leu Pro Ser Asp Phe Ser Arg Tyr Phe Gln
            180                 185                 190

Tyr Glu Gly Ser Leu Thr Thr Pro Pro Cys Ala Gln Gly Val Ile Trp
        195                 200                 205

Thr Val Phe Asn Gln Thr Val Met Leu Ser Ala Lys Gln Leu His Thr
    210                 215                 220

Leu Ser Asp Thr Leu Trp Gly Pro Gly Asp Ser Arg Leu Gln Leu Asn
225                 230                 235                 240

Phe Arg Ala Thr Gln Pro Leu Asn Gly Arg Val Ile Glu Ala Ser Phe
                245                 250                 255

Pro
```

<210> SEQ ID NO 10
<211> LENGTH: 59
<212> TYPE: PRT
<213> ORGANISM: Homo sapiens

<400> SEQUENCE: 10

```
Ser Ala Ser Glu Glu Pro Ser Pro Ser Glu Val Pro Phe Pro Ser Glu
1               5                   10                  15

Glu Pro Ser Pro Ser Glu Glu Pro Phe Pro Ser Val Arg Pro Phe Pro
            20                  25                  30

Ser Val Val Leu Phe Pro Ser Glu Glu Pro Phe Pro Ser Lys Glu Pro
        35                  40                  45

Ser Pro Ser Glu Glu Pro Ser Ala Ser Glu Glu
    50                  55
```

<210> SEQ ID NO 11
<211> LENGTH: 7

```
<212> TYPE: PRT
<213> ORGANISM: Homo sapiens

<400> SEQUENCE: 11

Pro Gly Glu Glu Asp Leu Pro
1               5

<210> SEQ ID NO 12
<211> LENGTH: 36
<212> TYPE: PRT
<213> ORGANISM: Homo sapiens

<400> SEQUENCE: 12

Gly Glu Glu Asp Leu Pro Ser Glu Glu Asp Ser Pro Arg Glu Glu Asp
1               5                   10                  15

Pro Pro Gly Glu Glu Asp Leu Pro Gly Glu Glu Asp Leu Pro Gly Glu
            20                  25                  30

Glu Asp Leu Pro
        35

<210> SEQ ID NO 13
<211> LENGTH: 6
<212> TYPE: PRT
<213> ORGANISM: Homo sapiens

<400> SEQUENCE: 13

Gly Glu Glu Asp Leu Pro
1               5

<210> SEQ ID NO 14
<211> LENGTH: 4
<212> TYPE: PRT
<213> ORGANISM: Homo sapiens

<400> SEQUENCE: 14

Glu Glu Asp Leu
1

<210> SEQ ID NO 15
<211> LENGTH: 5
<212> TYPE: PRT
<213> ORGANISM: Homo sapiens

<400> SEQUENCE: 15

Glu Glu Asp Leu Pro
1               5

<210> SEQ ID NO 16
<211> LENGTH: 6
<212> TYPE: PRT
<213> ORGANISM: Homo sapiens

<400> SEQUENCE: 16

Glu Asp Leu Pro Ser Glu
1               5

<210> SEQ ID NO 17
<211> LENGTH: 7
<212> TYPE: PRT
<213> ORGANISM: Homo sapiens

<400> SEQUENCE: 17

Glu Glu Asp Leu Pro Ser Glu
1               5
```

<210> SEQ ID NO 18
<211> LENGTH: 6
<212> TYPE: PRT
<213> ORGANISM: Homo sapiens

<400> SEQUENCE: 18

Asp Leu Pro Gly Glu Glu
1               5

<210> SEQ ID NO 19
<211> LENGTH: 6
<212> TYPE: PRT
<213> ORGANISM: Homo sapiens

<400> SEQUENCE: 19

Glu Glu Asp Leu Pro Ser
1               5

<210> SEQ ID NO 20
<211> LENGTH: 6
<212> TYPE: PRT
<213> ORGANISM: Homo sapiens

<400> SEQUENCE: 20

Gly Glu Asp Asp Pro Leu
1               5

<210> SEQ ID NO 21
<211> LENGTH: 16
<212> TYPE: PRT
<213> ORGANISM: Homo sapiens

<400> SEQUENCE: 21

His Pro Gln Arg Leu Pro Arg Met Gln Glu Asp Ser Pro Leu Gly Gly
1               5                   10                  15

<210> SEQ ID NO 22
<211> LENGTH: 24
<212> TYPE: PRT
<213> ORGANISM: Homo sapiens

<400> SEQUENCE: 22

Glu Glu Asp Ser Pro Arg Glu Glu Asp Pro Pro Gly Glu Glu Asp Leu
1               5                   10                  15

Pro Gly Glu Glu Asp Leu Pro Gly
            20

<210> SEQ ID NO 23
<211> LENGTH: 21
<212> TYPE: PRT
<213> ORGANISM: Homo sapiens

<400> SEQUENCE: 23

Asn Asn Ala His Arg Asp Lys Glu Gly Asp Asp Gln Ser His Trp Arg
1               5                   10                  15

Tyr Gly Gly Asp Pro
            20

<210> SEQ ID NO 24
<211> LENGTH: 540
<212> TYPE: DNA
<213> ORGANISM: Homo sapiens
<220> FEATURE:

```
<221> NAME/KEY: promoter
<222> LOCATION: (1)..(540)

<400> SEQUENCE: 24
cttgcttttc attcaagctc aagtttgtct cccacatacc cattacttaa ctcaccctcg      60
ggctccccta gcagcctgcc ctacctctt  acctgcttcc tggtggagtc agggatgtat     120
acatgagctg ctttccctct cagccagagg acatgggggg ccccagctcc cctgcctttc     180
cccttctgtg cctggagctg gaagcaggc  cagggttagc tgaggctggc tggcaagcag     240
ctgggtggtg ccagggagag cctgcatagt gccaggtggt gccttgggtt ccaagctagt     300
ccatggcccc gataaccttc tgcctgtgca cacacctgcc cctcactcca ccccatcct      360 agctttggta tgggggagag ggcacagggc cagacaaacc tgtgagactt tggctccatc     420
tctgcaaaag ggcgctctgt gagtcagcct gctcccctcc aggcttgctc ctcccccacc     480
cagctctcgt ttccaatgca cgtacagccc gtacacaccg tgtgctggga cacccccacag   540

<210> SEQ ID NO 25
<211> LENGTH: 7
<212> TYPE: PRT
<213> ORGANISM: Homo sapiens

<400> SEQUENCE: 25

Gly Val Ser Tyr Arg Pro Ala
1               5

<210> SEQ ID NO 26
<211> LENGTH: 7
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 26

Gly Val Xaa Tyr Xaa Pro Ala
1               5

<210> SEQ ID NO 27
<211> LENGTH: 4
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid

<400> SEQUENCE: 27

Tyr Xaa Xaa Met
1

<210> SEQ ID NO 28
<211> LENGTH: 7
<212> TYPE: PRT
<213> ORGANISM: Homo sapiens

<400> SEQUENCE: 28

Gly Val Ser Phe Arg Pro Ala
1               5
```

```
<210> SEQ ID NO 29
<211> LENGTH: 35
<212> TYPE: DNA
<213> ORGANISM: Homo sapiens

<400> SEQUENCE: 29 caaaggggt gtgagcttcc gcccagcaga ggtag                          35

<210> SEQ ID NO 30
<211> LENGTH: 35
<212> TYPE: DNA
<213> ORGANISM: Homo sapiens

<400> SEQUENCE: 30
ctacctctgc tgggcggaag ctcacacccc ctttg                         35

<210> SEQ ID NO 31
<211> LENGTH: 74
<212> TYPE: PRT
<213> ORGANISM: Homo sapiens

<400> SEQUENCE: 31

Gly Ser Ser Gly Glu Asp Asp Pro Leu Gly Glu Glu Asp Leu Pro Ser
1               5                   10                  15

Glu Glu Asp Ser Pro Arg Glu Glu Asp Pro Pro Gly Glu Glu Asp Leu
            20                  25                  30

Pro Gly Glu Glu Asp Leu Pro Gly Glu Glu Asp Leu Pro Glu Val Lys
        35                  40                  45

Pro Lys Ser Glu Glu Glu Gly Ser Leu Lys Leu Glu Asp Leu Pro Thr
    50                  55                  60

Val Glu Ala Pro Gly Asp Pro Gln Glu Pro
65                  70
```